United States Patent [19]

Kozak et al.

[11] Patent Number: 5,460,974
[45] Date of Patent: Oct. 24, 1995

[54] METHOD OF ASSAYING WHOLE BLOOD FOR HDL CHOLESTEROL

[75] Inventors: Mary B. Kozak, Osceola; Andrea Badke, Bristol, both of Ind.

[73] Assignee: Miles Inc., Elkhart, Ind.

[21] Appl. No.: 959,400

[22] Filed: Oct. 13, 1992

[51] Int. Cl.⁶ .................. G01N 33/92; G01N 1/18; G01N 21/77
[52] U.S. Cl. .................. 436/71; 436/169; 436/170; 436/177; 472/56; 472/57; 435/11
[58] Field of Search .................. 422/56, 57, 73; 435/11; 436/13, 71, 86, 169, 170, 177

[56] References Cited

U.S. PATENT DOCUMENTS

| | | | |
|---|---|---|---|
| 3,092,465 | 6/1963 | Adams et al. | 436/169 X |
| 3,146,163 | 8/1964 | Brewer | 422/101 X |
| 3,298,789 | 1/1967 | Hast | 436/95 |
| 3,552,925 | 1/1971 | Fetter | 436/169 |
| 3,552,928 | 1/1971 | Fetter | 436/169 X |
| 3,607,093 | 9/1971 | Stone | 422/56 |
| 4,045,176 | 8/1977 | Proksch et al. | 436/13 |
| 4,059,405 | 11/1977 | Sodickson et al. | 436/71 X |
| 4,126,416 | 11/1978 | Sears | 436/71 |
| 4,144,306 | 3/1979 | Figueras | 422/56 |
| 4,188,188 | 2/1980 | Willner et al. | 436/86 X |
| 4,190,628 | 2/1980 | Sears | 422/61 |
| 4,234,317 | 11/1980 | Lucas et al. | 436/177 X |
| 4,256,693 | 3/1981 | Kondor et al. | 422/56 |
| 4,258,001 | 3/1981 | Pierce et al. | 422/56 |
| 4,366,244 | 12/1982 | Pascal | 435/11 |
| 4,409,106 | 10/1983 | Furuta et al. | 436/177 X |
| 4,477,575 | 10/1984 | Vogel et al. | 436/177 |
| 4,544,630 | 10/1985 | Ziegenhorn et al. | 435/11 |
| 4,678,757 | 7/1987 | Rapkin et al. | 436/169 |
| 4,746,605 | 5/1988 | Kerscher et al. | 435/7 |
| 4,753,776 | 6/1988 | Hillman et al. | 422/101 |
| 4,761,381 | 8/1988 | Blatt et al. | 436/165 |
| 4,774,192 | 9/1988 | Ferminiello et al. | 422/56 X |
| 4,786,603 | 11/1988 | Wiellinger et al. | 422/56 X |
| 4,801,687 | 1/1989 | Ngo | 530/387 |
| 4,810,394 | 3/1989 | Masuda | 436/177 X |
| 4,816,224 | 3/1989 | Vogel et al. | 436/170 X |
| 4,883,765 | 11/1989 | Tamir et al. | 435/11 X |
| 4,892,815 | 1/1990 | Kerscher et al. | 436/71 X |
| 5,064,541 | 11/1991 | Jeng et al. | 436/177 X |
| 5,110,724 | 5/1992 | Hewett | 435/11 |
| 5,118,613 | 6/1992 | McGowan | 436/177 X |
| 5,135,716 | 8/1992 | Thakore | 436/71 X |
| 5,135,719 | 8/1992 | Hillman et al. | 436/177 X |
| 5,139,685 | 8/1992 | de Castro et al. | 436/170 X |
| 5,186,843 | 2/1993 | Baumgardener et al. | 436/177 X |
| 5,215,886 | 6/1993 | Patel et al. | 436/170 X |
| 5,262,067 | 11/1993 | Wilk et al. | 422/73 X |

FOREIGN PATENT DOCUMENTS

| | | |
|---|---|---|
| 0088420 | 7/1983 | European Pat. Off. |
| 0143574 | 1/1984 | European Pat. Off. |
| 0295526 | 6/1988 | European Pat. Off. |
| 0269240 | 6/1988 | European Pat. Off. |
| 0415298 | 3/1991 | European Pat. Off. |
| 0428980 | 5/1991 | European Pat. Off. |
| 3117455 | 2/1981 | Germany. |
| 8805912 | 8/1988 | WIPO. |

OTHER PUBLICATIONS

Clackson et al., "Precipitation of Serum Lipoproteins by Anionic Polyelectrolytes and Bivalent Cations", Monographs on Atherosclerosis, vol. II, 1982, pp. 17–39.

*Primary Examiner*—Donald E. Czaja
*Assistant Examiner*—Milton I. Cano
*Attorney, Agent, or Firm*—Roger N. Coe

[57] ABSTRACT

An improved device and method of a) separating the cellular components of whole blood from plasma or serum, b) separating the low density lipoprotein (LDL) fraction and the very low density lipoprotein (VLDL) fraction from the plasma or serum, then c) assaying the plasma or serum for cholesterol present in the high density lipoprotein (HDL) fraction are disclosed. The device includes a separation area that separates the cellular components of whole blood from the serum or plasma and separates the LDL and VLDL fractions from the serum or plasma, and a test area that assays the serum or plasma for the concentration of the HDL cholesterol. The method includes introducing a whole blood sample to a test device including a separation area comprising a first zone that separates the cellular components of the whole blood from the plasma or serum; and a second zone that separates the LDL and the VLDL fractions from the plasma or serum. The essentially cell-free, LDL-free and VLDL-free plasma or serum then migrates to a test area. After the plasma or serum migrates to the test area, plasma or serum is assayed for HDL cholesterol and the test area is examined for a quantitative response to HDL cholesterol present in the whole blood sample.

18 Claims, 6 Drawing Sheets

METHOD OF ASSAYING WHOLE BLOOD FOR HDL CHOLESTEROL

FIELD OF THE INVENTION

The present invention relates to an improved device and method of a) separating the cellular components of whole blood from the plasma or serum, b) separating the low density lipoprotein (LDL) fraction and the very low density lipoprotein (VLDL) fraction from the plasma or serum, and c) then assaying the plasma or serum for a predetermined constituent, like cholesterol, present in the high density lipoprotein (HDL) fraction. More particularly, the present invention relates to an improved method of separating the cellular components, the LDL fraction and the VLDL fraction from a whole blood sample by utilizing a device having a separation area including a first zone that separates and retains the cellular components of the whole blood sample from the plasma or serum, and a second zone that separates the LDL and the VLDL fractions from the plasma or serum. The undiluted plasma or serum that exits the separation area then migrates to a test area that includes the reagents necessary to assay the plasma or serum for cholesterol. After the undiluted plasma or serum contacts the test area, the test area is examined for a response, such as a color change, to provide a quantitative assay for HDL cholesterol present in the plasma or serum. In one embodiment, the device is a dry phase test strip wherein a separation area, comprising one or more filter pads, is in contact with a test area comprising a test pad. A surface of the test pad is examined for a response. In another embodiment, the separation area is in fluid communication with the test area, such that the cell-free, LDL-free and VLDL-free plasma or serum migrates from the separation area, such as through a capillary, to the test area to assay the HDL fraction for cholesterol in the test sample.

BACKGROUND OF THE INVENTION

Presently, numerous test devices are available to simply and rapidly analyze body fluids for the presence or absence of a predetermined soluble constituent. For example, tests are available to detect glucose, uric acid or protein in urine; and to detect glucose, triglycerides, potassium ion or cholesterol in blood. Historically, assays of a whole blood sample for a predetermined soluble constituent are the most difficult tests to design.

The cellular components of whole blood, and especially the red blood cells, are the primary interfering substances in assays for a soluble constituent of whole blood. Most simple blood tests are chromogenic, whereby a predetermined soluble constituent of the whole blood interacts with a particular reagent either to form a uniquely-colored compound as a qualitative indication of the presence or absence of the constituent, or to form a colored compound of variable color intensity as a quantitative indication of the presence of the constituent. The deep red color of the whole blood sample interferes with these chromogenic tests, and therefore the highly-colored red blood cells usually are separated from the plasma or serum before the blood sample is assayed for a predetermined soluble constituent.

The presence of red blood cells also can interfere with various nonchromogenic blood assays, whereby the assay results are either inconsistent or, if consistent, are inaccurate. Furthermore, other cellular components, including the white blood cells, also can interfere in standard chromogenic blood assays. Therefore, to achieve a reliable assay for a predetermined soluble constituent of whole blood, it is essential to separate the serum or plasma from the cellular components of whole blood prior to analyzing the whole blood sample for the predetermined soluble constituent.

The assay is further complicated when the predetermined soluble constituent of interest is cholesterol. All cells require cholesterol for growth, but an excess accumulation of cholesterol by the cells can cause various diseases, including atherosclerosis. Therefore, cholesterol is an important analyte because the amount of total serum cholesterol can be correlated to the incidence of atherosclerosis. Accordingly, the assay for cholesterol in serum or plasma is one of the most frequently performed tests in clinical laboratories.

Cholesterol and cholesterol esters are water-insoluble substances, and therefore are carried in the circulatory system by lipoproteins for eventual utilization by the cells. Lipoproteins are complex particles and contain varying amounts of proteins, phospholipids, cholesterol and triglycerides. The lipoproteins in serum are classified by their density. These density-based classes include very low density lipoproteins (VLDL), low density lipoproteins (LDL), and high density lipoproteins (HDL). Each of these lipoprotein classes carry varying amounts of cholesterol, and a total serum cholesterol assay is a complex average of the amount that each lipoprotein class contributes to the total lipoprotein concentration of the serum.

It is well-known that a specific lipoprotein class, the LDL fraction, is responsible for the accumulation of cholesterol in cells, and is more closely associated with the progression of heart disease, including atherosclerosis. Therefore, the early detection of increased levels of the LDL fraction in blood is of great importance. In contrast, the HDL fraction has been shown to be important in the removal of excess cholesterol from cells. Accordingly, a negative correlation exists between atherosclerosis and HDL cholesterol levels. Additionally, the correlation between atherosclerosis and the level of LDL cholesterol in the blood is higher than a similar correlation between atherosclerosis and total serum cholesterol levels.

High density lipoproteins (HDL) have been the focus of extensive investigation because of the inverse relationship between HDL cholesterol and the risk of heart infarction. Consequently, if the level of HDL cholesterol in the blood is low, an individual has an increased risk of heart infarction. Thus, the atherosclerosis risk of an individual can be estimated by assaying for HDL cholesterol. The HDL cholesterol assay then is used to calculate the approximate amount of strongly atherogenic LDL cholesterol from the formula:

$$LDL\ cholesterol = total\ cholesterol - \tfrac{1}{5}\ total\ triglycerides - HDL\ cholesterol.$$

In order to determine the cholesterol content of the HDL fraction, the other lipoprotein fractions must be removed from the test sample. Four general methods have been developed to separate the lipoprotein fractions. However, each method possesses disadvantages. For example, ultracentrifugation is a common method, but this method is unsuitable for routine laboratory assays because the method requires special equipment, a sensitive manipulative technique and a long separation time that can reach days. Consequently, ultracentrifugation has been restricted to medical research laboratories.

In another method, LDL content is determined by a fractional precipitation reaction utilizing a polyanion, such as heparin sodium or dextran sulfate, and a divalent cation, such as calcium, manganese or magnesium. In this method, the lipoprotein fractions are precipitated in the sequence VLDL, LDL, then HDL, by increasing the concentration of the polyanion. However, this process requires two manipulative steps because the VLDL fraction first is separated in a first precipitation step, then the LDL fraction is precipitated by increasing the concentration of the polyanion. Therefore, the process is impractical and is not amenable to automation.

In the third method, LDL cholesterol is determined from the Friedewald formula. Triglyceride and total cholesterol concentration, including HDL cholesterol content, of the sample is determined by precipitating the VLDL and LDL fractions from the test sample. The amount of LDL cholesterol then is calculated by the Friedewald formula. This method also is laborious and impractical. The fourth method, the electrophoretic separation and polyanion precipitation method, is time-consuming and requires the use of an electrophoresis apparatus and a densitometer for determining LDL cholesterol concentration. Accordingly, not one of the four above-described methods is suitable for the routine assay of HDL cholesterol.

In the assay of a whole blood sample for the amount of cholesterol in the HDL fraction, the cellular components of the whole blood, and the LDL and VLDL fractions of the plasma or serum, are separated from the whole blood sample. Conventionally, the plasma or serum is separated from the cellular material of whole blood by centrifugation. The cellular material collects at the bottom of the centrifuge tube and the supernatant plasma or serum is decanted. Accordingly, the interfering cellular components of whole blood are sufficiently removed such that a substantial background interference is avoided. The supernatant plasma or serum then is subjected to one of the above-described methods of separating the LDL and VLDL fractions from the plasma or serum.

The centrifuge method however has the major disadvantages of requiring a relatively large blood sample, usually from about 0.1 ml to about 5 ml, and requiring a long centrifuge time of approximately 5 to 10 minutes. Furthermore, the centrifuge method requires several manipulative steps. Consequently, a laboratory technician either can contact a potentially-infectious blood sample or can contact laboratory equipment contaminated by the relatively large blood sample, then contract a disease.

Overall, all the above-described separation techniques are best suited for large laboratories that assay a large number of blood samples, and for institutions, such as hospitals, that do not require assay results in a matter of minutes. However, many small laboratories and private medical offices do not have a centrifuge, ultracentrifuge or other such blood, plasma or serum separation devices on site. Therefore, simple chromogenic tests cannot be performed quickly, safely and easily on site, and the whole blood sample is sent to an outside laboratory for efficient and safe separation and assay. As a result, the assay results are available in hours or days as opposed to minutes.

Accordingly, investigators have continually sought a device and method of quickly, safely and easily separating essentially all of the interfering cellular components of whole blood from the plasma or serum such that the identity and concentration of soluble constituents in the plasma or serum are not altered. In addition, for cholesterol assays, a need also exists for a simple and inexpensive device and method of separating the LDL and VLDL fractions from the plasma or serum such that a physician can provide an individual a better estimation of a potential cardiovascular risk than the estimation provided by present day total serum cholesterol assays. Investigators have provided several methods and devices for separating the interfering cellular components and the LDL and VLDL fractions from the plasma or serum. However, each method and device possessed at least one disadvantage that made the method or device inaccurate, cumbersome or impractical in assaying a whole blood sample for the cholesterol present in the HDL fraction of the serum or plasma.

Methods other than centrifugation have been used to separate the cellular components of a small whole blood sample from the serum or plasma. One of the simpler methods, disclosed by Adams et al. in U.S. Pat. No. 3,092,465, used a bibulous, or moisture absorbing, matrix that is impregnated with a chromogenic testing reagent and coated with a semipermeable barrier. The semipermeable barrier screens the cellular components of the whole blood sample and permits passage of the smaller, soluble molecules and ions to contact the chromogenic testing reagent incorporated into the bibulous matrix. In the case of a positive test, the essentially colorless plasma or serum interacts with the chromogenic testing reagent to produce a color in the bibulous matrix. The color is observed by rinsing or wiping the cellular material retained on the semipermeable barrier from the test device. However, the rinsing or wiping technique is cumbersome and laborious, and assay interference is possible if the red blood cells are not completely wiped or rinsed from the semipermeable barrier. In addition, the possibility of technician contact with the potentially-infectious blood sample is high. Mast, in U.S. Pat. No. 3,298,789, disclosed a similar device, wherein a film of ethylcellulose is utilized as the semipermeable barrier. Sodickson, in U.S. Pat. No. 4,059,405, achieved separation of the cellular components from the blood plasma or serum with an ultrafiltration membrane.

Fetter U.S. Pat. Nos. 3,552,925 and 3,552,928 disclosed another method and device to assay whole blood samples for soluble constituents. Fetter described a test device having a bibulous matrix impregnated with a nonvolatile inorganic salt or an amino acid at a first region on the matrix and impregnated with a test reagent at an adjacent second region of the matrix. A whole blood sample is introduced onto the bibulous matrix such that the whole blood first contacts the first region of the bibulous matrix including the inorganic salt or amino acid. The salt or amino acid precipitates the cellular components from the blood, and the plasma or serum then migrates to the test reagent-impregnated second region of the bibulous matrix for a chromogenic interaction with the test reagent.

Another prior art method of separating the cellular components of whole blood from the plasma or serum was disclosed in Vogel et al. U.S. Pat. No. 4,477,575, describing a process and a composition for separating plasma or serum from whole blood using a layer of glass fibers having a defined average diameter and density. However, the amount of plasma or serum that can be separated is limited to at most 50%, and preferably less than 30%, of the absorption volume of the glass fibers. Otherwise, whole blood effectively clogs the glass fiber layer. Therefore, the method requires a high ratio of hydrophobic glass fibers to whole blood volume.

In other prior art methods, the whole blood is diluted before assaying for a predetermined soluble plasma or serum constituent. The dilution of whole blood is burdensome because an extra manipulative step is required, and dilution introduces the possibility of assay error because of an incorrect dilution of the blood sample. The possibility of technician contact with the potentially-infectious blood sample also is increased. For example, German Patent Publication DE-OS 34 41 149 disclosed a method of separating plasma or serum from whole blood by passing the whole blood through a lectin-impregnated matrix that is repeatedly rinsed with a diluent to dilute the plasma or serum before the assay is performed. The use of a lectin or a polymeric amino acid to separate the cellular material from a whole blood sample also is disclosed in European Patent Application No. 84307633.2.

In developing a method and device for separating and assaying small whole blood samples, a primary consideration is the degree of sophistication of the technician performing the assay. Often it is desirable to have relatively untrained personnel perform routine assays and obtain accurate quantitative results. Therefore, it is important that the assay method minimize manipulative steps, be free of possible interferences or contamination, minimize or eliminate the possibility of laboratory personnel physically contacting the blood sample, and provide for easy measurement. For example, among the several possible manipulative steps, the dilution of the whole blood, or the plasma or serum, prior to the actual assay introduces the most probable step for assay error or personal contact with the blood sample. Another common manipulative error is incomplete wiping or rinsing of the cellular components of whole blood from the surface of a device that utilizes a cell-impermeable membrane to separate the cellular components from the plasma or serum of whole blood.

Therefore, a need exists for a method and device to efficiently separate and accurately assay small volumes of whole blood. The method preferably avoids distinct manipulative steps to: 1) separate the cellular components from the plasma or serum, and then 2) to separate a particular component from the plasma or serum prior to the assay. Furthermore, in order to avoid dilution errors, the method preferably allows the assay of undiluted plasma or serum. It also is desirable to provide a blood separation and blood assay method that protects the technician from contact with the blood sample; that avoids the time delays of the present methods; that is independent of the hematocrit value of the blood sample; and that yields accurate and reproducible results.

The ideal method includes withdrawing a whole blood sample in a "noninvasive" amount, such as a pin prick drop, and immediately depositing the undiluted whole blood sample on a test device that separates the cellular components from the undiluted plasma or serum; that separates an undesirable or interfering component from the plasma or serum; and that then assays the undiluted plasma or serum, absent the undesirable component, like the LDL and VLDL fractions, for the presence or concentration of a predetermined soluble constituent, like HDL cholesterol, within minutes. Alternatively, the test device can contact a fresh puncture wound and withdraw a fresh, undiluted blood sample from the wound for analysis. Such a separation and assay method and device allow medical personnel to perform whole blood analyses on a more routine and more confident basis.

Consequently, investigators have attempted to develop test devices that include an element to separate, collect and retain the cellular components of whole blood. Examples of such attempts are disclosed in Vogel et al. U.S. Pat. No. 4,477,575; Rothe et al. U.S. Pat. No. 4,604,265; Kennedy et al. application PCT/US86/02192; Rapkin et al. U.S. Pat. No. 4,678,757; Terminiello et al. U.S. Pat. No. 4,774,192; Stone U.S. Pat. No. 3,607,093; Figueras U.S. Pat. No. 4,144,306; and Pierce et al. U.S. Pat. No. 4,258,001.

Each of the above-identified patents is directed to separating the cellular components of whole blood from the plasma or serum. However, the resulting plasma or serum includes the HDL, the LDL and the VLDL fractions. Therefore, it is still necessary to separate the HDL fraction in the serum or plasma from the LDL and the VLDL fractions in order to accurately determine the amount of HDL cholesterol in the whole blood sample. Some investigators attempted to avoid this second separation by assaying for HDL cholesterol in the plasma or serum indirectly, such as from the difference between the total cholesterol concentration and the sum of cholesterol in the LDL and the VLDL fractions, or by a similar indirect method.

For example, Ziegenhorn et al., in U.S. Pat. No. 4,544,630, disclose a method of assaying for cholesterol in the LDL fraction in the presence of the HDL fraction by a direct enzymatic determination under conditions wherein the LDL fraction interacts with the enzymatic reagents substantially more quickly than the HDL fraction. Sears, in U.S. Pat. Nos. 4,126,416 and 4,190,628, discloses methods and assay kits for LDL cholesterol in blood plasma by separating the LDL cholesterol from the other fractions by agglutinating the LDL fraction with a plant lectin, then detecting the amount of cholesterol in the agglutinated LDL fraction. Sears discloses that either the cholesterol in the LDL fraction can be assayed or, alternatively, the cholesterol in the supernatant liquid, including the HDL and the VLDL fractions can be assayed, then the LDL cholesterol concentration can be determined indirectly.

German Patent Publication DE-OS 31 17 455 discloses a precipitating reagent including phosphotungstic acid and magnesium ions to precipitate the LDL and the VLDL fractions. The cholesterol in the HDL fraction of the supernatant fluid then can be determined. If the total cholesterol concentration of the test sample is known, the HDL cholesterol assay is used in an indirect method of assaying for LDL cholesterol. Not one of the above-identified references teaches or suggests a method or device wherein the test sample is the whole blood, and wherein the cellular components of the whole blood first are separated from the whole blood sample, followed by separation of the LDL and the VLDL fractions from the HDL fraction, in order to assay for HDL cholesterol without a separate precipitating, centrifuging or diluting step. As will be demonstrated more fully hereinafter, the present invention provides a method and a device to assay a small sample of whole blood without time consuming manipulative steps that expose a technician to a potentially-infected test sample and that lead to assay errors.

McGowan, in U.S. Pat. No. 5,118,613, discloses determination of HDL lipoprotein constituents using a whole blood sample. First, the whole blood sample is anticoagulated with a compound like ethylenediaminetetraacetic acid. The LDL and VLDL fractions then are precipitated from the anticoagulated whole blood by magnesium ions and dextran sulfate. The LDL fraction, VLDL fraction and cellular material are separated from the solution by centrifuging, and the supernatant solution, including essentially the entire HDL fraction, is assayed for an HDL constituent, like cholesterol. This method includes the time-consuming and potentially infectious manipulative step of centrifuging.

Other investigators have disclosed devices for assaying blood wherein manipulative diluting and centrifuging steps are eliminated. For example, Kondo et al., in U.S. Pat. No. 4,256,693, disclose a multi-layered device to assay for various serum components, such as cholesterol. The Kondo et al. device includes a filter layer for removing the cellular components of whole blood. The filter layer is positioned over a water-proof layer having at least one small opening. The plasma or serum exiting the filter layer passes through the small opening of the water-proof layer first to contact a spreading layer, then to contact a test area. The analyte of interest then interacts with reagents included in the test area, and a detectable response is observed through the bottom of the device. The device of Kondo et al. cannot measure for HDL cholesterol because all the lipoprotein fractions exit the filter layer to eventually saturate the test area. Accordingly, only total cholesterol is assayed by the device of Kondo et al. device. In addition, and as will be demonstrated more fully hereinafter, the Kondo et al. device does not include a capillary tube, an important feature of the present invention.

Blatt et al., in U.S. Pat. No. 4,761,381, disclose a volume metering device, including a capillary channel, for metering a liquid sample to a reaction chamber. In the Blatt et al. device, the test sample is not filtered. Therefore, in an assay of whole blood, the cellular material interferes in a chromogenic assay for cholesterol because of uneven color development and hematocrit interference in high hematocrit regions. Furthermore, the lipoprotein fractions are not separated, thereby precluding an assay of the whole blood sample for HDL cholesterol.

Hillman et al., in U.S. Pat. No. 4,753,776, disclose a blood separation device that includes a filter and a capillary channel to channel the plasma or serum exiting the filter to a reaction area. Hillman et al. do not teach or suggest further separating the VLDL and LDL fractions from the plasma or serum to provide a method and device to assay for HDL cholesterol.

European Patent Application 168,093 discloses a binder for the LDL fraction. The binder is a sulfated polyvinyl alcohol crosslinked to a water-insoluble substrate. The EPO Application however does not teach separating the cellular components of whole blood from the plasma or serum, followed by separating the lipoprotein fractions in a method to assay for HDL cholesterol. Kerscher et al. U.S. Pat. No. 4,746,605 teaches precipitating the HDL fraction from a test sample, followed by assaying the supernatant liquid for the LDL fraction. In contrast, the present method and device assay the plasma or serum for HDL cholesterol after first separating the cellular components and then separating the LDL fraction and the VLDL fraction from the plasma or serum.

Therefore, because of the disadvantages present in the above-discussed methods and test devices, it is apparent that a simple and effective method of separating the cellular components of whole blood to provide essentially cell-free, unaltered and undiluted plasma or serum, and of separating an undesirable or interfering component of the plasma or serum prior to assaying the plasma or serum for a predetermined analyte, like HDL cholesterol, is needed. Accordingly, the method of the present invention allows the safe, accurate and economical assay of a whole blood sample for HDL cholesterol by utilizing a test device having a separation area including a first zone that separates and retains the cellular components of the whole blood sample from the plasma or serum, and a second zone that separates the LDL fraction and the VLDL fraction from the plasma or serum. The second zone is in intimate contact with, or is in fluid communication with, a test area incorporating the necessary reagents to assay for HDL cholesterol. The plasma or serum exits the separation area in an undiluted form, then migrates to the test area. At the test area, an interaction between the HDL cholesterol and the assay reagents produces a detectable response, such as a color transition, that is free from interferences attributed to highly-colored cellular components and to cholesterol present in the LDL and the VLDL fractions.

The method and device of the present invention allow the assay of whole blood for HDL cholesterol without resorting to a lengthy and expensive extra manipulative step of centrifuging or diluting the test sample. The plasma or serum that saturates the test pad is essentially free of cellular material, the VLDL fraction and the LDL fraction, and is unaltered and undiluted, thereby allowing an accurate and trustworthy assay for HDL cholesterol. The method and device of the present invention also eliminate the disadvantages of hematocrit sensitivity; technique sensitivity due to wiping or rinsing the cellular components from the test device; and disposal of the cellular components.

In accordance with one embodiment of the present invention, after the whole blood sample has passed through the separation area to saturate the test area, a test pad, saturated with undiluted plasma or serum essentially free of the VLDL and the LDL fractions, then is examined for a response to HDL cholesterol by standard dry phase chemistry test strip procedures. In a preferred embodiment, the separation area is not removed from the test device, and a surface of the test pad free from contact with the separation area is examined for a response, such as by examination through a transparent support.

In accordance with another embodiment of the present invention, the separation area and the test area are not in intimate contact, but are in fluid communication by means of a capillary. In this embodiment, the essentially cell-free, LDL-free and VLDL-free plasma or serum migrates from the separation area of the device through a capillary to the test area of the device for an assay of HDL cholesterol in the test sample. The separation area comprises a first zone to remove the cellular components of the whole blood sample and a second zone to remove the VLDL and LDL fractions from the plasma or serum.

In accordance with another important feature of the present invention, the device precludes contact between the technician and the whole blood sample. The blood sample is absorbed into the separation area in such a manner that excess blood sample does not remain on an outside surface of the device. In addition, the technician need not wipe or rinse the cellular components from the device before examination of the device for a response. Consequently, the device essentially eliminates the possibility of contact between the technician and a potentially-infectious blood sample.

As a result of the present invention, the assay of plasma or serum for HDL cholesterol is accurate and reliable because the interferences attributed to the highly-colored cellular components and the LDL and VLDL fractions are essentially eliminated. Prior methods and devices relied upon separating the cellular components from the blood sample by centrifuging, and precipitating and centrifuging the LDL and VLDL fractions from the blood sample. Then, the serum or plasma was assayed for HDL cholesterol by a wet chemistry procedure that was time consuming and required manipulation of the sample and reagents. As will be demonstrated more fully hereinafter, the device of the present invention provides a fast, accurate and economical method of assaying a whole blood sample for HDL cholesterol in the solid or the liquid phase, whereby sample dilutions, reagent and serum manipulation, and technician contact with the blood sample are eliminated.

The separation area utilized in the present invention effectively separates the cellular components from a whole blood sample by utilizing a first separation zone including a filter pad or a portion of a filter pad, that optionally incorporates a relatively small amount of a separating reagent composition, such as an agglutinin, like a lectin; a coagulant, like a thrombin or a thrombin-like compound; or a combination thereof. The optional separating reagent composition incorporated into the first zone of the separation area does not effect the concentration of the lipoprotein fractions in the serum or plasma.

The separation area effectively separates the LDL and VLDL fractions from the serum or plasma by utilizing a second separation zone, including a filter pad or a portion of a filter pad, that incorporates a precipitating reagent composition comprising a polyvalent metal ion, like magnesium ion, and a precipitating compound, like dextran sulfate, therein. Accordingly, undiluted and cell-free serum or plasma including the HDL fraction then migrates to the test area for an assay of HDL cholesterol. Furthermore, the serum or plasma is distributed evenly throughout the entire test pad to provide a homogeneous assay response throughout the test area of the device.

In accordance with an important feature of the present invention, the method and device provide an assay for EDL cholesterol that eliminates wet phase precipitation and centrifugation steps; that eliminates technician handling of the test sample; that eliminates test sample dilution and similar manipulative steps; that utilizes a small blood sample volume; and that eliminates corrections for hematocrit differences between blood samples. Consequently, the test device of the present invention is more economical; separates essentially all of the cellular components and the VLDL and LDL fractions from a whole blood sample; and provides fast, more consistent and more reproducible assays for HDL cholesterol.

SUMMARY OF THE INVENTION

In brief, the present invention is directed to a device and method of separating the cellular components and the LDL and VLDL fractions from a whole blood sample, then assaying the undiluted serum or plasma for HDL cholesterol without additional manipulative steps. Separating the cellular components and the LDL and VLDL fractions of whole blood from the plasma or serum by the method and device of the present invention provides an undiluted serum or plasma sample for an accurate assay of HDL cholesterol. The separation method and assay device do not introduce contaminants into the serum or plasma, and do not adversely alter the compositional makeup of the plasma or serum.

In accordance with an important feature of the present invention, the device includes a separation area that separates the cellular components and the LDL and VLDL fractions of whole blood from the serum of plasma. In one embodiment, the separation area is in intimate contact with a test pad that assays the undiluted serum or plasma for HDL cholesterol. In another embodiment, the separation area of the device is in fluid communication with the test area by means of a capillary. The separation area includes a first zone to Separate the cellular components from the whole blood sample and a second zone to separate the soluble LDL and VLDL fractions from the plasma or serum.

The separation area preferably includes one or more filter pads. In one embodiment of the present invention, the first zone of the separation area is a filter pad comprising a suitable carrier matrix optionally incorporating therein a separating reagent composition to assist separating the cellular blood components from the serum or plasma. In accordance with the present invention, the filter pad of the first separation zone effectively separates the cellular components from the whole blood sample, thereby precluding the cellular components from interfering with a chromogenic assay for a HDL cholesterol in the serum or plasma.

The serum or plasma, in an undiluted and unaltered form, migrates from the first separation zone to a second separation zone comprising a filter pad that effectively separates the LDL and VLDL fractions from the plasma or serum, without separating the HDL fraction from the plasma or serum. The serum or plasma, including the HDL fraction, then migrates to a test area, and is assayed for HDL cholesterol by a reagent composition incorporated into the test area. The method and device also essentially preclude technician contact with a potentially-infectious blood sample. In an alternative embodiment, the separation area includes a single filter pad wherein one portion of the filter pad comprises the first separation zone and a second portion of the filter pad comprises the second separation zone.

In one embodiment of the present invention, the separation area and the test area of the device are in intimate contact, such that the plasma or serum exiting the second zone of the separation area migrates directly to the test area. The test area includes the reagents necessary to assay for HDL cholesterol, and a response then is monitored. In another embodiment, the separation area and the test area are in fluid communication by means of a capillary. At the separation area, the cellular components, the VLDL fraction and the LDL fraction are separated from the test sample. The undiluted plasma or serum then migrates through the capillary to the test area of the device. The plasma or serum is collected at the test area, and is allowed to interact with the reagents necessary for the assay of HDL cholesterol. The necessary reagents can be introduced to the test area either before or after the plasma or serum is collected. The test area of the device then is examined for a response to determine the HDL cholesterol concentration of the blood sample.

The present invention eliminates technique dependence from the assay, such as eliminating the manipulative steps of precipitation and centrifugation, and also assures that the proper volume of plasma or serum contacts the test area of the device. Furthermore, technician contact with the potentially-infectious blood sample is essentially precluded. An alternative assay method for HDL cholesterol is envisioned wherein the collected serum or plasma is withdrawn from the device, such as with a pipette, then is assayed for HDL cholesterol by well-known dry phase or wet phase diagnostic techniques.

The method consisting essentially of first contacting a whole blood sample with a test device comprising: (a) a separation area including a first zone to separate the cellular components of whole blood and a second zone to separate the soluble LDL and VLDL fractions from the blood, and (b) a test area, incorporating a reagent composition, to assay for HDL cholesterol. As used here, and hereinafter, the expression "reagent composition" is defined as a chemical or mixture of chemicals causing a detectable interaction upon contact with HDL cholesterol.

The whole blood sample initially contacts the first zone of the separation area. The first separation zone comprises a carrier matrix or a portion of a carrier matrix, and optionally includes a reagent to assist in separating the cellular components from the whole blood sample. The whole blood sample permeates through the first separation zone, wherein the red blood cells and other cellular and particulate components of the whole blood are separated from the plasma or serum through the action of the carrier matrix and the optional separating reagent composition. The undiluted and unaltered plasma or serum continues to permeate through the first zone to contact a second zone that is in contact with the first zone.

The second separation zone comprises a carrier matrix or a portion of a carrier matrix, and includes a precipitating reagent composition that effectively separates the LDL and VLDL fractions from the plasma or serum, but essentially does not alter the concentration of the HDL fraction in the plasma or serum. The plasma or serum continues to permeate through the second separation zone either to contact a test area that is in contact with the second zone or is in fluid communication, such as via a capillary, with the second zone to deliver the plasma or serum to the test area of the device. Optionally, a third zone is included in the separation area of the test device. The third zone comprises a carrier matrix or a portion of a carrier matrix and is not treated with a reagent. The third zone serves to remove the final traces of the cellular components, the LDL fraction and the VLDL fraction from the plasma or serum.

The assay of interest is performed at the test area of the device. The undiluted plasma or serum interacts with the indicator reagent composition to produce a detectable, and preferably a measurable, change in the test area, such as a color change, to show the presence of HDL cholesterol, or to permit a quantitative determination of HDL cholesterol. The test area then is examined, either visually or by instrument, for a qualitative or quantitative response to the HDL cholesterol present in the test sample. Consequently, the assay for HDL cholesterol is achieved by using a simple and inexpensive test device that effectively separates the interfering cellular components and the VLDL and LDL fractions from the blood sample without manipulative steps that can lead to technician error or technician contact with a potentially-infectious blood sample.

Therefore, the present invention is directed to a method and device for (a) rapidly and effectively separating the cellular components from the plasma or serum of undiluted whole blood, (b) separating the LDL and VLDL fractions from the plasma or serum, and (c) then assaying the plasma or serum for HDL cholesterol. More particularly, and in accordance with an important feature of the present invention, at least two zones of a separation area are arranged to separate the cellular components and the LDL and VLDL fractions from whole blood and to allow the plasma or serum including the HDL fraction to migrate to a test area that either is in contact with, or is connected via a capillary to, the separation area. After the test area is saturated with plasma or serum, the plasma or serum interacts with a reagent composition, then the test area is examined for a qualitative or quantitative response to HDL cholesterol. Accordingly, assay interferences attributed to the cellular components and to the LDL and VLDL fractions of whole blood are eliminated, thereby achieving a more accurate and more reliable serum or plasma assay for HDL cholesterol.

In accordance with an important feature of the present invention, a whole blood sample contacts a test device comprising a separation area including a first separation zone and a second separation zone. The first zone comprises a suitable carrier matrix, and optionally incorporated therein is a cell-separating reagent composition comprising an agglutinin, like a lectin; a coagulant, like a thrombin or a thrombin-like compound; or a mixture thereof, to assist in separating the cellular components from the whole blood sample. To achieve the full advantage of the present invention, the whole blood sample contacts a first separation zone comprising a suitable carrier matrix incorporating a separating reagent composition comprising a lectin. The first zone achieves separation of the cellular components of the whole blood from the plasma or serum and does not add interfering ions or molecules to, or remove soluble constituents from, the serum or plasma.

The plasma or serum then migrates by gravity to a second zone of the separation area. The second separation zone comprises a suitable carrier matrix incorporating therein a precipitating reagent composition comprising a polyvalent metal ion, preferably a divalent metal ion, and a precipitating compound to separate the soluble LDL and VLDL fractions from the plasma or serum. To achieve the full advantage of the present invention, the plasma or serum contacts a second separation zone including a suitable carrier matrix incorporating a precipitating reagent composition comprising magnesium as the polyvalent metal ion and dextran sulfate as the precipitating compound. The second zone achieves separation of the LDL and VLDL fractions from the plasma or serum, and does not add interfering ions or molecules to, or remove the HDL fraction from, the serum or plasma.

In accordance with another important feature of the present invention, the serum or plasma including the HDL fraction contacts a test area of the device and is assayed for HDL cholesterol by reagents well-known in the art of diagnostic assays. The test area can be in intimate contact with the separation area of the device, or the test area can be in fluid communication with the separation area by means of a capillary. If the separation area and the test area are in intimate contact, the device can be configured into an economical test strip that can be used by medical personnel, or by an individual at home, to quickly and accurately determine HDL cholesterol levels in the blood.

Therefore, an important aspect of the present invention is to provide a method and device to quickly and effectively separate the cellular components and the LDL and VLDL fractions from the plasma or serum of small whole blood samples, then to assay the plasma or serum for HDL cholesterol. The method and device allow the rapid, easy and effective separation of the cellular components and the LDL and VLDL fractions of whole blood from the serum or plasma, such that the plasma or serum can be assayed for HDL cholesterol without additional manipulative steps. Accordingly, interferences attributed to the cellular components and the LDL and VLDL fractions of whole blood in assays of undiluted and unaltered plasma or serum for HDL cholesterol are eliminated. Furthermore, the assay is independent of the amount of hematocrit in the blood sample. Therefore, assay corrections for hematocrit differences are eliminated.

A new and improved test device of the present invention can assay, qualitatively or quantitatively, a small sample volume of whole blood for HDL cholesterol and essentially eliminate assay interferences attributed to the cellular components and the soluble LDL and VLDL fractions of the whole blood sample. The test device for assaying an undiluted whole blood sample for HDL cholesterol comprises (a) a separation area including a first zone to remove the cellular components of the whole blood, and a second zone to remove the LDL and VLDL fractions from the plasma or serum; and (b) a test area incorporating an indicator reagent composition in intimate contact with, or in fluid communication with, the separation area to assay the plasma or serum for HDL cholesterol.

In one embodiment, the test area of the device comprises a substrate material capable of homogeneously incorporating a reagent composition that interacts with the HDL cholesterol in the serum or plasma. In this embodiment, the second zone of the separation area is in intimate contact with the test pad, and comprises a suitable carrier matrix having incorporated therein a precipitating reagent composition comprising a polyvalent metal ion and a precipitating compound, that interacts with, and separates, the LDL and VLDL fractions from the plasma or serum. The first zone of the separation area is in contact with the second zone, and comprises a suitable carrier matrix optionally having incorporated therein a separating reagent composition comprising a lectin, a thrombin or a thrombin-like compound that interacts with, and helps separate the cellular components of a whole blood sample from the plasma or serum. Accordingly, the separation area and the test area can be configured in a multilayered array to provide a dry phase test strip to assay for HDL cholesterol.

In another embodiment, the test area is in fluid communication with the separation area by means of a capillary. The plasma or serum including the HDL fraction exits the separation area and is introduced to the test area by means of a capillary. The plasma or serum can be collected in the test area for subsequent assay, or can be assayed immediately. The new and improved test device and method of assaying for the presence or concentration of HDL cholesterol in whole blood can be performed in the home by an untrained individual because the assay is fast and reproducible, requires a small volume of blood and is independent of hematocrit concentration of the blood sample, thereby eliminating the need to correct assay results for hematocrit differences.

BRIEF DESCRIPTION OF THE DRAWINGS

The above and other aspects, advantages and novel features of the present invention will become apparent from the following detailed description of the preferred embodiments of the present invention taken in conjunction with the following figures wherein.

DETAILED DESCRIPTION OF THE INVENTION

Figure 1:
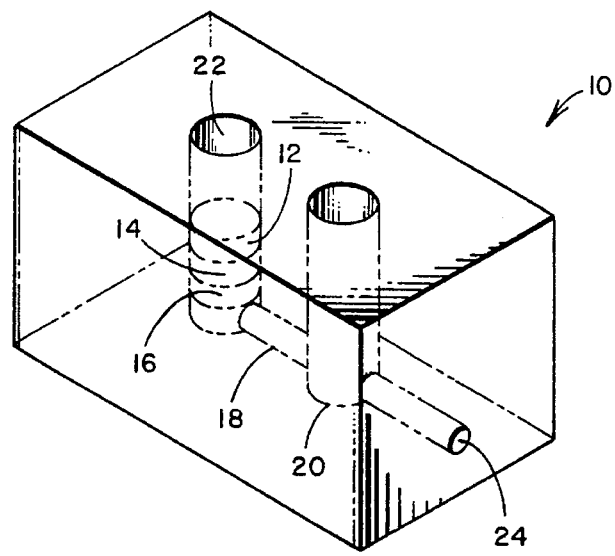
FIG. 1 is a perspective view of a test device of the present invention wherein a separation area to separate the cellular components of a whole blood sample from the plasma or serum and to separate the VLDL and LDL fractions in the plasma or serum from the HDL fraction, and a test pad to assay the plasma or serum for HDL cholesterol are connected by a capillary.

In accordance with the method of the present invention, the cellular components of a whole blood sample first are separated from the plasma or serum; then, the LDL and VLDL fractions are separated from the undiluted and unaltered plasma or serum; next the plasma or serum is assayed for HDL cholesterol without any further manipulative steps. According to the method and device of the present invention, a small blood sample, usually a pin prick amount, is sufficiently large to achieve separation of the cellular components and the VLDL and LDL fractions, and to assay the serum or plasma for HDL cholesterol, as opposed to the milliliter size blood samples required in the centrifuge method of separating cellular components from whole blood and the ultracentrifuge method of separating the LDL and VLDL fractions from plasma or serum. Furthermore, the method and device of the present invention eliminate manipulative steps, like dilution, that can cause technician error or technician contact with a potentially-infectious whole blood sample.

Surprisingly and unexpectedly, the test device of the present invention essentially completely separates the highly-colored and interfering red blood cells and the VLDL and LDL fractions from the plasma or serum, and then assays the plasma or serum for HDL cholesterol, within minutes, without the additional time-consuming and potentially unhealthful manipulative steps of precipitation, centrifugation, decantation or dilution. The method of the present invention provides rapid and reliable assays on small samples of whole blood, e.g., about 20 μL (microliters), that include up to about 65% hematocrit with a simple and inexpensive device. Overall, the method and device of the present invention are ideally suited for routine blood assays at home, in small laboratories and in private medical offices, wherein the number of assays is relatively low, but accurate results nevertheless are required in a short time period.

As will become apparent from the following detailed description of the invention, the method and device of the present invention are suited especially for assays utilizing a chromogenic response to determine the presence or concentration of the various soluble constituents of whole blood. Therefore, it is of primary importance to remove the highly-colored red blood cells from the whole blood sample in order to achieve an accurate and reliable detection and measurement of the chromogenic response. Furthermore, it is also important to remove the interfering LDL and VLDL fractions from the essentially cell-free plasma or serum in the assay for HDL cholesterol.

Any method or device for separating the cellular components of whole blood from the plasma or serum, and the LDL and VLDL fractions from the serum or plasma, should quickly and efficiently achieve cell, LDL fraction and VLDL fraction separation; remove only the cellular components, the LDL fraction and the VLDL fraction and not the HDL fraction; avoid contamination of the plasma or serum with interfering ions or molecules; and minimize or eliminate hemolysis, wherein the red blood cells rupture and release highly-colored components to the plasma or serum. Due to the potentially infectious nature of the blood sample, the method and device also should minimize, or eliminate, human contact with the blood sample.

In accordance with an important feature of the present invention, the cellular components of whole blood are effectively separated from the essentially colorless plasma or serum by allowing the whole blood sample to contact and permeate through a separation area having a first zone comprising a suitable carrier matrix, like a filter pad. The carrier matrix optionally includes a separating reagent composition. The separating reagent composition comprises an agglutinin, like a lectin; or a coagulant, like a thrombin or a thrombin-like compound; or a mixture thereof. The separating reagent composition enhances the inherent ability of the carrier matrix to remove the highly-colored cellular components from the whole blood sample to yield a straw-colored plasma or serum that is amenable to a simple and accurate determination of its soluble components.

The undiluted and unaltered straw-colored plasma or serum then is directed by gravity to a second zone of the separation area. The second separation zone comprises a suitable carrier matrix, like a filter pad, having a precipitating reagent composition incorporated therein to remove the LDL and VLDL fractions from the plasma or serum. The plasma or serum contacts and permeates through the second separation zone, and the precipitating reagent composition, comprising: 1) a polyvalent metal ion, preferably a divalent metal ion, like magnesium ion, and 2) a precipitating compound, like dextran sulfate, removes the VLDL and LDL fractions from the plasma or serum, but does not remove the HDL fraction from the plasma or serum. Optionally, an untreated third zone of the separation area is positioned to receive the plasma or serum exiting the second zone. The third zone removes the final traces of the cellular components and the LDL and VLDL fractions from the serum or plasma.

The final zone of the separation area, i.e., the second or third zone, can be in intimate contact with a test area of the device, or can be in fluid communication with the test area of the device, such as by a capillary. If the final zone intimately contacts the test area, the test area generally comprises a test pad. Accordingly, in one embodiment, as the whole blood permeates through the first separation zone, the cellular components are separated from the whole blood sample, and are collected and retained in the first zone. The unaltered serum or plasma then advances to, and saturates, a second separation zone that is in laminar contact with the first zone and that precipitates and removes the LDL and VLDL fractions from the plasma or serum. The plasma or serum containing the HDL fraction then advances to, and saturates, a test pad that is in laminar contact with the second separation zone, or, if present, the optional third separation zone. The test pad comprises a suitable substrate material incorporating therein a reagent composition that interacts with HDL cholesterol to give a detectable or measurable response. After the test pad is saturated by the plasma or serum, the test pad is examined for a response, such as a chromogenic response, either visually or by instrument, to the HDL cholesterol present in the plasma or serum.

In another embodiment, the test area is not in contact with the second zone, or with the optional third zone, but is in fluid communication with the separation area of the device by means of a capillary. In this embodiment, the plasma or serum including the HDL fraction exits the separation area of the device and enters a capillary. The capillary collects the serum or plasma, then the capillary delivers the serum or plasma to a test area of the device wherein the serum or plasma is collected and assayed for HDL cholesterol. The test area can include a reagent composition to assay for HDL cholesterol, or a reagent composition can be added to the collected serum or plasma at a later time in order to assay for HDL cholesterol.

Generally, the first zone of the separation area of the present invention comprises a carrier matrix that has an inherent ability to filter the cellular components from a whole blood sample. Preferably, the carrier matrix, such as a filter pad, has an inherent ability to filter essentially all of the cellular components from a whole blood sample. The carrier matrix normally is a hydrophilic, absorbent matrix capable of separating the cellular components of whole blood from the plasma or serum, and is amenable to incorporating an optional separating reagent composition to facilitate the essentially complete separation of the cellular components from the whole blood sample. In addition to collecting and retaining the separated cellular components, the carrier matrix permits the plasma or serum to permeate through the first separation zone essentially unimpeded and unaltered to contact the second zone of the separation area.

The carrier matrix of the first zone also should permit the blood sample to permeate through the first zone at a sufficient rate to allow adequate time for efficient red blood cell separation, yet rapidly enough to obtain blood assays relatively quickly. In addition, the carrier matrix should not promote hemolysis, contaminate the serum or plasma by serum or plasma-extraction of components of the carrier matrix, remove serum or plasma constituents by chemical or physical interactions, or appreciably alter the undiluted plasma or serum in a way to make the subsequent assay for HDL cholesterol inconclusive, inaccurate or doubtful.

Preferably, the first zone of the separation area comprises a hydrophilic carrier matrix possessing the above-mentioned characteristics, and a separating reagent composition. The carrier matrix allows the blood to move, in response to capillary forces, through the first zone. The cellular components are separated from the plasma or serum by the separating reagent composition and the carrier matrix, and are retained by the first filter pad. The essentially unaltered serum or plasma then continues advancing through the first separation zone to contact and saturate a second separation zone that is in contact with the first zone.

The carrier matrix can be any hydrophilic material that allows only the essentially cell-free and straw-colored plasma or serum to pass through the first zone to eventually contact the test area for analysis of HDL cholesterol. Suitable hydrophilic carrier matrices include bibulous and non-bibulous, fibrous and nonfibrous matrices, like hydrophilic inorganic powders, such as silica gel, alumina, diatomaceous earth and the like; sponge materials; argillaceous substances; cloth; hydrophilic natural polymeric materials, particularly cellulosic material, like cellulosic beads, and especially fiber-containing papers such as filter paper or chromatographic paper; and synthetic or modified naturally occurring polymers, such as cellulose acetate, polyvinyl chloride, polyacrylamide, a polyacrylate, a polyurethane, crosslinked dextran, agarose and other such crosslinked and noncrosslinked water-insoluble hydrophilic polymers. Similarly, other suitable carrier matrices include fibrous and nonfibrous matrices, like a glass fiber matrix; and synthetic polymers, like polypropylene, polyethylene, nylon, polyvinylidene fluoride or a polysulfone. A hard, porous plastic also is useful as the carrier matrix as long as the plastic is sufficiently porous to allow the plasma or serum to permeate through the plastic and contact the test area.

Therefore, the carrier matrix of the first separation zone has a pore size of between about $0.1\mu$ (micron) and about $50\mu$, and preferably between about $0.3\mu$ and about $10\mu$, to achieve efficient separation of the cellular components and to permit the serum or plasma to advance through the first zone. To achieve the full advantage of the present invention, the carrier matrix has a pore size ranging from about $0.5\mu$ to about $8\mu$.

The first zone of the separation area can include more than one carrier matrix, and the carrier matrices can have different physical characteristics and can be different chemical compositions or a mixture of chemical compositions. The carrier matrix, or matrices, of the first zone also can vary in regards to smoothness and roughness combined with hardness and softness. However, in every instance, the carrier matrix, or matrices, of the first zone separates and retains the cellular components of whole blood, and allows the plasma or serum to pass through the first zone unaltered and essentially unimpeded. Therefore, regardless of the exact composition of the carrier matrix, or matrices, the primary considerations are separation of the cellular components of a whole blood sample, collection and retention of the cellular components of whole blood, transmittal of substantially unaltered and undiluted plasma or serum and incorporation of an optional separating reagent composition.

To achieve the full advantage of the present invention, the carrier matrix comprises a cellulosic material, such as paper and preferably filter paper; or a glass fiber matrix. Both a filter paper and a glass fiber matrix possess the properties required of a suitable carrier matrix of the present invention, plus the advantages of abundant supply, favorable economics and a variety of suitable grades. Furthermore, filter paper and glass fiber matrices are capable of suspending and positioning an optional separating reagent composition in the first filter pad, and of separating the cellular components from whole blood.

As known to those skilled in the art, filter paper and glass fiber matrices are available in a variety of thicknesses and porosities. Since the device requires that the first separation zone contact the whole blood sample, and that a substantially colorless fluid must be allowed to emerge therefrom, the thickness and porosity of the carrier matrix influence the efficiency of the test device and influence the effectiveness of the separation process. The thickness and porosity of the first zone are directly related to the inherent ability of the carrier matrix to separate the cellular components from plasma or serum and to the time required for the whole blood sample to permeate through the first zone to separate the cellular components from the whole blood sample. Therefore, if a carrier matrix of high porosity is used, the thickness of the carrier matrix should be sufficient to allow a minimum effective contact time between the whole blood and the first zone in order to achieve an effective separation of the cellular components of the whole blood. Conversely, if a carrier matrix of low porosity is utilized, a relatively thin layer of carrier matrix can be employed. The proper balance between carrier matrix porosity and thickness, and a judicious selection of the type and concentration of optional separating reagent incorporated into the carrier matrix, is well within the experimental techniques used by those skilled in the art of preparing a test device described in the present specification.

A first separation zone comprising an untreated carrier matrix often cannot completely separate the cellular components from whole blood. If a sample of whole blood is applied to an untreated filter paper matrix, the amount of separated cellular components observed as the whole blood sample permeates through the filter paper varies with the thickness and porosity of the filter paper. For other carrier matrices, only a partial separation of the cellular components from a whole blood sample has been observed as the blood permeates through a carrier matrix having sufficient thickness and sufficiently low porosity. However, separation of the cellular components of whole blood from plasma or serum is not observed if the carrier matrix is too thin or too porous. But, if a carrier matrix incorporates, or otherwise is treated with, a suitable separating reagent composition, the cellular components are effectively separated and fixed in the carrier matrix as the blood sample permeates through the first separation zone.

An untreated carrier matrix having a thickness of at least about 1 mm (millimeter), and usually of at least about 1.5 mm, is sufficient to effectively separate the cellular components from a whole blood sample. If an optional separating reagent composition is incorporated into the carrier matrix to remove the cellular components from the serum of plasma, the thickness of the carrier matrix can be reduced to as low as about 0.2 mm, and preferably as low as about 0.3 mm. Therefore, to achieve the full advantage of the present invention, the first filter pad comprises a carrier matrix in the form of a pad, having dimensions of, for example, about 0.25 cm. (centimeters) to about 1 cm by about 0.5 cm to about 2 cm and a thickness of about 0.2 mm to about 0.8 mm, having incorporated therein a separating reagent composition comprising an agglutinin, like a lectin; a coagulant, like a thrombin or a thrombinolike compound; or a mixture thereof. A first separation zone comprising a filter pad of such dimensions has sufficient length, width and thickness for effective separation of cellular components within a sufficiently short time after the blood contacts one end, or the top, of the filter pad.

The undiluted and unaltered plasma or serum that emerges from the carrier matrix of the first separation zone then contacts a second separation zone. The second zone of the separation area comprises a carrier matrix incorporating a precipitating reagent composition to separate the LDL and VLDL fractions from the serum or plasma. The carrier matrix of the second zone possesses the same physical and chemical properties described above in regard to the carrier matrix of the first zone. Accordingly, the carrier matrix of the second zone can be constructed from any of the materials described above in regard to the carrier matrix of the first zone. The carrier matrix of the second zone also can possess the same physical characteristics of the carrier matrix of the first zone, such as pore size and matrix thickness, and can be identical to the carrier matrix of the first zone. The pore size preferably between about $1\mu$ and about $50\mu$ to achieve efficient separation of the LDL and VLDL fractions from the serum of plasma.

In every case, the carrier matrix of the second separation zone incorporates a precipitating reagent composition to separate the VLDL and LDL fractions from the plasma or serum, essentially without effecting the concentration of the HDL fraction in the serum or plasma. The precipitating reagent composition incorporated into the carrier matrix of the second separation zone comprises a polyvalent metal ion, preferably a divalent metal ion, like magnesium ion, and a precipitating compound, like dextran sulfate. The precipitating reagent composition interacts with the LDL and VLDL fractions in the serum or plasma to form a precipitate that is collected and retained in the carrier matrix of the second zone. The carrier matrix permits the plasma or serum containing the soluble HDL fraction to permeate through the second separation zone essentially unimpeded to contact the test area of the device.

If a test device of the present invention includes filter pads of the above-defined dimensions as the carrier matrix for first and second separation zones, a pin-prick amount of blood, such as about 20 µL (microliters), usually is a sufficient amount of sample to provide a fast and accurate assay for HDL cholesterol. It also has been found that the blood sample can include up to about 65% hematocrit and no assay corrections for hematocrit are necessary. The blood sample can be applied to the test device dropwise or with a pipette. Preferably, if the test device is a dry phase test strip, the test device contacts a fresh puncture wound and the blood sample is drawn into the test device by capillary action. In accordance with another feature of the present invention, the amount of whole blood sample contacting the test device need not be precisely measured. However, care should be exercised to avoid overloading the separation area of the test device with an excessively large blood sample such that a portion of whole blood contacts the test area of the test device.

As will be discussed more fully hereinafter, the first zone of the separation area comprises a carrier matrix that preferably incorporates an optional separating reagent composition to achieve an essentially complete separation of the cellular components of whole blood from the plasma or serum. Therefore, in accordance with an important feature of the present invention, a separating reagent composition comprising an agglutinin, a coagulant or a mixture thereof is incorporated into the carrier matrix such that the cellular components of the whole blood agglutinate or are trapped as the blood sample chromatographs through the first zone. The agglutinated or trapped cells become fixed, and are collected within the first separation zone, as the plasma or serum continues advancing through the separation area to eventually contact and saturate the test pad of the test device.

As will become apparent from the following detailed description of the invention, various lectins, thrombins or thrombin-like compounds, used individually or in combination, agglutinate or coagulate the cellular components within the carrier matrix, and allow the undiluted serum or plasma to advance, unaltered and essentially unimpeded, to the second zone of the separation area. In addition, the lectins, thrombins or thrombin-like compounds present in the separating reagent composition do not promote excessive hemolysis. Therefore, the red blood cells do not rupture, and highly-colored components do not interfere with and mask the chromogenic assays.

The preferred agglutinin present in the separating reagent composition is a lectin. The lectins are proteins or glycoproteins that are known to agglutinate, or clump, cells and precipitate complex carbohydrates. Lectins are isolated from a wide variety of natural sources, including seeds, plant roots, bark, fungi, bacteria, seaweed, sponges, fish eggs, invertebrate and lower vertebrate body fluids, and mammalian cell membranes. The lectins used in the present invention preferably are not specific to a particular blood group, or the general utility of the method and device of the present invention could be limited. Therefore, lectins showing no specificity of blood grouping and that are suitable for use in the present invention include, but are not limited to, *Abrus precatorius* (abrin, Jequirty bean), *Agaricus bisporous* (mushroom), *Bauhinia purpurea* (camels foot tree), *Caragana arborescens* (Siberian pea tree), *Cicer arietinum* (chick pea), *Codium fragile* (Green marine algae), *Canavalia ensiformis* (Con A, Concanavalin A, Jack bean), *Datura stramonium* (jimson weed), *Glycine max* (Soybean), *Lathyrus odoratus* (Sweet Pea), *Lens culinaris* (Lentil), *Limulus polyphemus* (Horseshoe crab, Limulin), *Lycopersicon esculentum* (Tomato), *Maclura pomifera* (Osage orange), *Mycoplasma gallisepticum, Naja mocambique mocambique* (cobra venom), *Naja naja kaouthia* (cobra venom), *Perseau americana* (Avocado), *Phaseolus coccineus* (Scarlet runner bean), *Phaseolus vulgaris* (Red Kidney bean), *Phytolacca americana* (Pokeweed), *Pisum sativum* (garden pea), *Pseudomonas aeruginosa, Psophocarpus tetragonolobus* (winged bean), *Ricinus communis* (Castor bean), *Robinia pseudoacacia* (black locust, false acacia), *Sambucus nigra* (elder), *Solanum tubersum* (Potato), *Triticum vulgaris* (Wheat germ), *Vicia faba* (fava bean, broad bean), *Vicia sativa, Vigna radiata* (Mung bean), *Viscum album* (European mistletoe), *Wisteria floribunda* (Japanese wisteria), and other like, nonblood specific lectins.

The preferred lectins incorporated into the carrier matrix of the first separation zone are the lectin from Concanavalin A (jack bean), the lectin from *Solanum tubersum* (potato), the lectin from *Triticum vulgaris* (wheat germ), the lectin from *Bauhinia purpurea* (camels foot tree) and the lectin from *Phytolacca americana* (pokeweed). To achieve the full advantage of the present invention, the first separation zone has incorporated therein the lectin from potato or the lectin from pokeweed.

In addition to, or in place of, the above-described lectins, a coagulant can be used to separate the cellular components of whole blood from the serum or plasma. Specifically, the enzyme thrombin, from bovine plasma, has been incorporated into a carrier matrix to provide a first zone of the separation area that successfully separates serum or plasma from whole blood samples. The bovine thrombin effectively promotes blood clotting such that the red blood cells are removed from the whole blood as the blood permeates through the first separation zone. Other thrombins useful according to the method of the present invention include, but are not limited to, human thrombin, horse thrombin, goat thrombin, mouse thrombin, rat thrombin, pig thrombin, sheep thrombin and mixtures thereof.

Furthermore, in addition to, or in place of, the above-described lectins and thrombins, a coagulant that behaves similar to a thrombin can be used to effect separation of the serum or plasma from the cellular components of whole blood. Such thrombin-like compounds include, but are not limited to, the enzymes acutase, agkistrodon contortrix, ancrod, atroxin, crotalase and combinations thereof. Such compounds are thrombin-like in behavior and effectively promote blood clotting. It is not necessary to immobilize the thrombin, the lectin or the thrombin-like compound onto the carrier matrix, and that an effective separation of the cellular components from a whole blood sample can be achieved by using a lectin, a thrombin, a thrombin-like compound or a mixture thereof.

As previously described, the device of the present invention also includes a second separation zone, comprising a carrier matrix incorporating therein a precipitating reagent composition to separate the LDL and VLDL fractions from the serum or plasma exiting the first separation zone, without effecting the HDL fraction in the serum or plasma. The precipitating reagent composition incorporated into the carrier matrix of the second zone comprises a polyvalent metal ion, such as a divalent metal ion, like calcium ion, magnesium ion or manganese ion, and a precipitating compound, like dextran sulfate, heparin sodium, phosphotungstic acid or polyvinyl sulfate. The preferred polyvalent metal ion is a divalent metal ion, such as magnesium ion, and the preferred precipitating compound is dextran sulfate.

A suitable precipitating reagent composition interacts with essentially only the VLDL and LDL fractions and does not alter the concentration of another soluble plasma constituent, like HDL cholesterol; is not appreciably extracted by the plasma or serum from the second separation zone and thereby transferred to the test area of the device; and does not otherwise interfere in the assay for HDL cholesterol.

To achieve the full advantage of the present invention, the polyvalent metal ion is incorporated into the carrier matrix as a water-soluble salt, typically as a chloride salt. Other suitable anions of the water-soluble polyvalent metal salt include, but are not limited to, nitrate, bromide and organic anions, like acetate. In general, any polyvalent metal ion that separates the LDL and VLDL fractions from serum or plasma, without effecting the HDL fraction, can be included in the precipitating reagent composition. To achieve the full advantage of the present invention, the polyvalent metal ion is a divalent metal ion. Suitable divalent metal ions include, but are not limited to, magnesium, calcium, manganese, cobalt, strontium, zinc, barium, copper and mixtures thereof. Calcium, magnesium and manganese are the preferred divalent metal ions. Other suitable polyvalent metal ions having a valence greater than two include, but are not limited to, aluminum, iron and chromium. The polyvalent metal ion is incorporated into the second separation zone from an aqueous solution that includes from about 10 mM to about 1000 mM, and preferably from about 20 mM to about 500 mM, of the polyvalent metal salt.

The precipitating reagent composition also includes a precipitating compound that interacts with the LDL and VLDL fractions in the serum or plasma in conjunction with the polyvalent metal ion. This interaction precipitates the LDL and VLDL fractions, but essentially does not effect the HDL fraction. The precipitate is retained in the carrier matrix of the second separation zone, whereas the HDL fraction continues to migrate through the second zone to contact the test area of the device.

In general any precipitating compound that separates the VLDL and the LDL fractions from the plasma or serum, without separating the HDL fraction, can be included in the precipitating reagent composition. Therefore, suitable precipitating compounds include, but are not limited to, dextran sulfate, heparin sodium, polyvinyl sulfate, phosphotungstic acid, sodium tungstate, ammonium molybdate and mixtures thereof. A preferred precipitating compound is dextran sulfate, phosphotungstic acid or mixtures thereof. The precipitating compound is incorporated into the second separation zone from an aqueous solution that includes from 0.1 g/L to about 20 g/L, and preferably from 5 g/L to about 15 g/L, of the precipitating compound. The precipitating compound and the polyvalent metal ion can be combined and incorporated into the second carrier matrix from the same aqueous solution, or can be incorporated from separate aqueous solutions.

Therefore, in summary, optionally incorporating an aqueous separating reagent composition including about 25 units to about 250 units of a lectin, or about 50 NIH units to about 150 NIH units of a thrombin or a thrombin-like compound, into a suitable carrier matrix provides a preferred first separation zone of the present invention. In addition, incorporating an aqueous precipitating reagent composition, comprising about 10 mM to about 1000 mM of a water-soluble polyvalent metal salt and about 0.1 g/L to about 20 g/L of a precipitating compound, into a suitable carrier matrix provides a second separation zone of the present invention. By arranging the first and second zones in a laminar array, whereby the whole blood sample first contacts the first zone, essentially all of the cellular components and essentially the entire LDL and VLDL fractions are separated from the plasma or serum, without effecting the HDL fraction. The resulting plasma or serum then can be assayed for HDL cholesterol.

Therefore, a more economical test device is provided because a whole blood sample can be assayed for HDL cholesterol without the need to perform manipulative steps such as dilution, precipitation and centrifugation. In addition, the assay method is safe because technician contact with a potentially infectious blood sample is essentially eliminated. More accurate and reproducible assay results also are achieved because blood samples including up to about 65% at hematocrit, i.e., cellular components, can be assayed for HDL cholesterol without the need to correct the assay for the amount of hematocrit. Accordingly, the method and device provide more sensitive and accurate assays for HDL cholesterol because the interfering effects of the cellular components and the LDL and HDL fractions are effectively eliminated.

In accordance with the method of the present invention, a whole blood sample contacts the separation area of the test device, whereby the cellular components of the whole blood are separated from the serum or plasma as the blood sample advances through the first zone of the separation area. The undiluted and unaltered serum or plasma advances through the first zone by gravity to contact and saturate a second zone of the separation that is in contact with the first zone. The second zone separates the LDL and VLDL fractions from the undiluted plasma or serum. In one embodiment, the plasma or serum including the HDL fraction advances through the second zone to contact and saturate a test area that is in intimate contact with the second zone. In another embodiment, the plasma or serum including the HDL fraction advances through the second separation zone and enters a capillary. The capillary directs the plasma or serum to a test area where the serum is collected and assayed for HDL cholesterol.

In each embodiment, the test area of the test device includes an indicator reagent composition suitable to assay for HDL cholesterol. In the first embodiment, e.g., a dry phase test strip, the indicator reagent composition is incorporated into a suitable substrate material, like filter paper. After the test area is saturated with the plasma or serum and the serum or plasma contacts the indicator reagent composition, the test area is examined, either visually or instrumentally, for a response to the HDL cholesterol in the plasma or serum.

The positioning of the separation zones in the separation area and of the test area in each embodiment is better understood by reference to FIGS. 1 through 4. FIG. 1 is a perspective view of a test device 10 including a separation area comprising a first separation zone 12 having a surface in contact with a first surface of a second separation zone 14. Second separation zone 14 has a second surface in contact with a surface of an optional third separation zone 16. Each separation zone can be a separate carrier matrix like filter paper, either untreated or treated with an appropriate reagent composition. Alternatively, the separation zones all can be present in a single carrier matrix of sufficient thickness wherein appropriate portions of the carrier matrix either are untreated or are treated with an appropriate reagent composition. Separation zones 12, 14 and 16 are arranged in a laminar array, and each zone is in contact with any adjacent separation zones. The separation area is in fluid communication with a test area 20 by means of a capillary 18. First zone 12 preferably has incorporated therein an optional separating reagent composition including an agglutinin or a coagulant. Second zone 14 has incorporated therein a precipitating reagent composition comprising polyvalent metal ion and a precipitating compound. Third zone 16 is untreated.

The serum or plasma exiting the separation area is introduced to test area 20 by capillary 18. Capillary 18 generally has a diameter of from about 5 mils to about 75 mils, and preferably from about 15 mils to about 50 mils. Test area 20 can have incorporated therein a suitable indicator reagent composition, or the indicator reagent composition can be introduced at a later time. As will be discussed more fully hereinafter, in order to facilitate the quantitative determination of HDL cholesterol, it is preferred that capillary 18 and test area 20 be manufactured from a hydrophilic material, preferably a transparent hydrophilic material.

A whole blood sample is introduced to test device 10 through a sample port 22 and a portion of the sample passes through separation zones 12, 14 and, if present, 16 to contact capillary 18. Capillary 18 collects the plasma or serum sample, then introduces the sample to test area 20. An air vent 24 facilitates passage of the sample through capillary 18 to test area 20.

After the essentially cell-free, LDL-free and VLDL-free plasma or serum contacts an indicator reagent composition in test area 20, an interaction between the indicator reagent composition and the HDL cholesterol produces a detectable change, like a chromogenic change, in test area 20. Test area 20 then is examined for the response, either visually or by instrument, and the intensity and degree of the response are correlated to the amount of HDL cholesterol in the blood sample. It is unnecessary to correct the response for the hematocrit value of the blood sample. The cellular components of the whole blood sample are fixed in first separation zone 12, and the LDL and VLDL fractions are fixed in second separation zone 14. Accordingly, these components of the whole blood sample do not interfere with the detectable change in test area 20.

Figure 2:
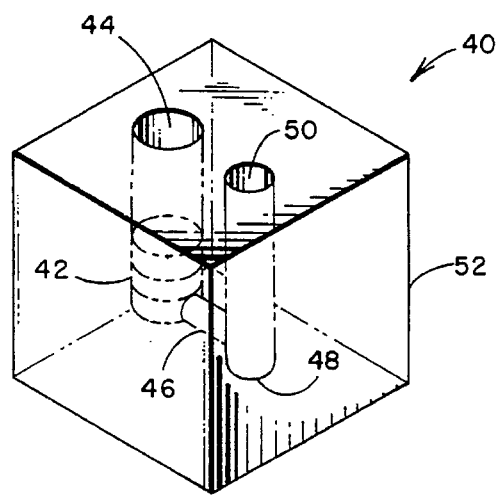
FIG. 2 is a perspective view of another embodiment of a test device of the present invention wherein a separation area and a test area are connected by a capillary.

Another, and preferred, configuration of a test device of the present invention is illustrated in FIG. 2, showing a test device 40 wherein first, second and optional third separation zones are arranged in a laminar configuration in a separation area 42 of test device 40. A whole blood sample is introduced to test device 40 at a sample port 44, and after separation of the cellular components and the LDL and VLDL fractions from the whole blood sample by the separation zones of separation area 42, the serum or plasma migrates through a capillary 46 to a test area 48. An air vent 50 facilitates passage of the serum or plasma through capillary 46 to test area 48. Test device 40 is designed such that test area 48 and separation area 42 are in different horizontal planes. Accordingly, unlike test device 10 of FIG. 1, capillary 46 of FIG. 2 is not arranged horizontally, but is aligned in a downward direction from separation area 42 toward test area 48. The plasma or serum passes through capillary 46 to contact the indicator reagent composition in test area 48. The presence or concentration of HDL cholesterol in the plasma or serum is determined by examining test area 48 for a detectable response through a transparent housing 52.

Figure 3:
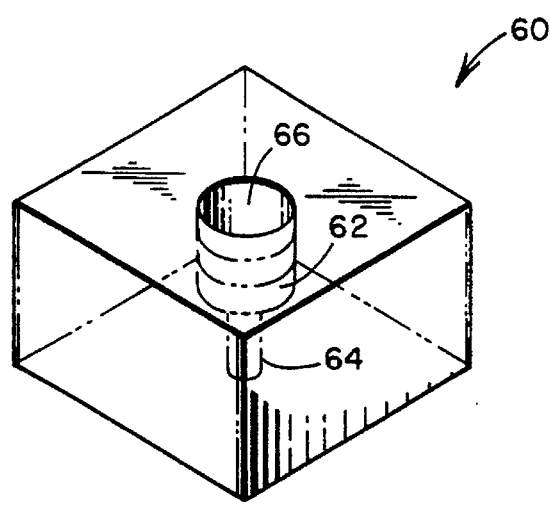
FIG. 3 is a perspective view of yet another embodiment of a test device of the present invention wherein a separation area is positioned above a capillary that collects the plasma or serum for the assay of HDL cholesterol.

Another embodiment of the present invention is illustrated in FIG. 3, showing a test device 60 including a separation area 62 that includes a laminar array of a first, second and, optionally, third separation zones. Separation area 62 is in contact with a capillary 64. A whole blood sample is introduced to test device 60 through a sample port 66 to contact and permeate through separation area 62. Separation area 62 separates the cellular components and the LDL and VLDL fractions from the whole blood sample, and the plasma or serum advances through separation area 62 to contact and fill capillary 64. After capillary 64 is filled with plasma or serum, the plasma or serum is assayed for HDL cholesterol, such as by dipping a test strip including the necessary reagents to assay for HDL cholesterol into the plasma or serum, or by contacting the plasma or serum with a solution of the reagents necessary to assay for HDL cholesterol. Then, visual or instrumental examination for a response to the reagents provides a determination of HDL cholesterol in the blood sample. Corrections for variations in hematocrit values are not necessary.

Figure 4:
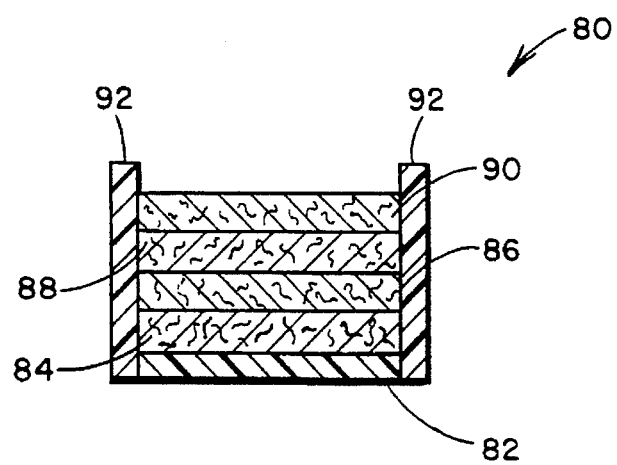
FIG. 4 is an end view of a test strip device of the present invention showing a laminar configuration of a first blood separating filter pad, a second filter pad for separating the VLDL and LDL fractions, an optional third filter pad and a test pad to assay for HDL cholesterol.

FIG. 4 is an end view of a dry phase test strip device 80 of the present invention. Test strip device 80 includes a hydrophobic strip or handle 82. A test pad 84 is adhesively secured to a surface of strip or handle 82. Test pad 84 has incorporated therein the reagents necessary to assay for HDL cholesterol. Test pad 84 therefore undergoes a detectable response upon contact with HDL cholesterol, and this response can be examined through strip or handle 82 manufactured from a transparent material.

An optional third separating filter 86 is adhesively secured to a surface of test pad 84 opposite the surface of test pad 84 adhesively secured to strip or handle 82. Third separating filter 86 comprises an untreated bibulous matrix, and serves as a final, optional filter to remove traces of cellular components or LDL or VLDL fractions that pass through filter pads 88 and 90.

A second filter pad 88 is adhesively secured to a surface of third separating filter 86 opposite the surface of third filter 86 adhesively secured to test pad 84. Second filter pad 88 comprises a carrier matrix incorporating the precipitating reagent composition and removes the LDL and VLDL fractions from the serum or plasma. Similarly, a first filter pad 90 is adhesively secured to a surface of second filter pad 88 opposite the surface of second filter pad 88 adhesively secured to separating filter 86. First filter pad 90 comprises a carrier matrix, and preferably incorporates an optional separating reagent composition to assist in the removal of the cellular components from a whole blood sample. The laminar array comprising strip or handle 82, test pad 84, third separating filter 86, second filter pad 88 and first filter pad 90 is strengthened by hydrophobic vertical supports 92.

In accordance with an important feature of the present invention, a whole blood sample first contacts first filter pad 90 of test device 80. The whole blood sample migrates through first filter pad 90, second filter pad 88 and optional third separating filter 86 to remove the cellular components and the LDL and VLDL fractions from the whole blood sample. The serum or plasma emerging from third separating filter 86 includes the HDL fraction. Upon contacting an indicator reagent composition incorporated into test pad 84, the serum or plasma undergoes a detectable response that can be examined through transparent strip or handle 82. Therefore, a rapid and accurate assay for HDL cholesterol can be accomplished without the time-consuming manipulative steps of dilution, precipitation and centrifugation. Eliminating such manipulative steps increases assay accuracy by eliminating the possibility of technician error and increases assay safety by eliminating the possibility of technician contact with a potentially infectious blood sample.

Several other alternative embodiments of test devices similar to the test devices illustrated in FIGS. 1–4 also are envisioned. For example, the separation area and test pad can vary relatively in size to account for a larger or a smaller blood sample, with the relative sizes of the separation area and test pad related to the blood sample size needed to accurately assay for HDL cholesterol.

EXAMPLE 1

INCORPORATING AN OPTIONAL SEPARATING REAGENT COMPOSITION INTO THE CARRIER MATRIX OF THE FIRST SEPARATION ZONE

The agglutinin, coagulant or mixture thereof, such as bovine thrombin, the lectin from *Solanum tuberosum*, the lectin concanavalin A, the lectin from *Phytolacca americana*, or the thrombin-like enzyme acutase, is solubilized in normal, or isotonic, saline solution. The separating reagent composition then is incorporated into a carrier matrix, such as filter paper, like WHATMAN CCP500 filter paper, or a glass fiber matrix, like WHATMAN PD107, available from Whatman Ltd., Maidenshead, Kent, U.K., either by immersing the carrier matrix into the separating reagent composition or by spraying the separating reagent composition onto sheets or precut strips of the carrier matrix. The carrier matrix incorporating the separating reagent composition then is dried at about 50° C. in an oven for about 20 minutes to about 40 minutes to provide a first separation zone of the present invention.

It is not necessary to immobilize the thrombin, thrombin-like compound or lectin onto the carrier matrix when incorporating the separating reagent composition into the carrier matrix as in Example 1. The simple drying technique is sufficient to maintain the lectin, thrombin or thrombin-like compound in place within the carrier matrix for separation of the cellular components from a whole blood sample. The carrier matrix of the first separation zone, after appropriate sizing, e.g., 0.5 cm × 1.0 cm, then is secured to the carrier matrix of the second separation zone, such as to the second separation zone 14 illustrated in FIG. 1, or to the second filter pad 88 illustrated in FIG. 4.

EXAMPLE 2

INCORPORATING THE PRECIPITATING REAGENT COMPOSITION INTO THE CARRIER MATRIX OF THE SECOND SEPARATION ZONE

The polyvalent metal ion salt and the precipitating compound were solubilized in water. The aqueous precipitating reagent composition then was incorporated into a carrier matrix, such as filter paper, like WHATMAN CCP500 filter paper, or a glass fiber matrix, like WHATMAN PD107, available from Whatman Ltd., Maidenshead, Kent, U.K., either by immersing the carrier matrix into the precipitating reagent composition or by spraying the precipitating reagent composition onto sheets or precut strips of the carrier matrix. The carrier matrix incorporating the precipitating reagent composition then was dried at about 50° C. in an oven for about 20 minutes to about 40 minutes to provide a second filter pad of the present invention.

To demonstrate the new and unexpected results achieved by the method and device of the present invention, dry phase test strips, as illustrated in FIG. 4 and including a transparent plastic handle, were prepared. Each test strip included a test pad comprising a filter paper substrate incorporating the test reagents necessary to assay for cholesterol. Each test strip also included a first filter pad comprising a glass fiber matrix having incorporated therein the lectin Solanum tuberosum. The lectin was incorporated into the glass fiber matrix from an aqueous separating reagent composition including 0.2 mg/mL (milligrams per milliliter) of the lectin Solanum tuberosum. The amount of lectin in the separating reagent composition is sufficient to incorporate from about 25 units to about 250 units of lectin per cubic centimeter of glass fiber matrix.

Each test strip also included a second filter pad comprising a filter paper matrix having incorporated therein a precipitating reagent composition comprising magnesium chloride and dextran sulfate. The precipitating reagent composition was incorporated into the filter paper matrix from an aqueous precipitating reagent composition including 10 g/L (grams per liter) of dextran sulfate and 500 mM (millimolar) magnesium chloride. Each test strip also included an optional third filter pad comprising untreated filter paper.

The test strips were used to assay blood samples including up to 65% hematocrit for HDL cholesterol.

In addition to the dry phase test strips, a device as illustrated in FIG. 2 was used to assay for HDL cholesterol in a whole blood sample. The first and second and third separation zones were filter pads prepared as described above. The filter pads were cut into 0.9 cm (centimeter) diameter circles and arranged in a stacked array of three filter pads. The blood sample first passed through the first filter pad to separate the cellular components, then through the second filter pad to separate the HDL and VLDL fractions, and finally through the third filter pad to remove the final traces of the cellular material, the LDL fraction and the VLDL fraction. The undiluted serum or plasma including the HDL fraction passed through the capillary and was collected. The serum or plasma then was analyzed on an OPTIMATE automatic analyzer, available from Miles, Inc., Elkhart, Ind., for HDL cholesterol by standard procedures known to those skilled in the art.

To demonstrate the ability of the above-described device to separate the interfering components from a whole blood sample and to assay the sample for HDL cholesterol, test samples including either a known or an unknown amount of HDL cholesterol were assayed using a device of the present invention illustrated in FIG. 2. The assay results were compared to results achieved by prior art precipitation and centrifugation methods. TABLE I illustrates the results of these experiments. Accordingly, TABLE I shows that the HDL cholesterol concentration determined by the method and device of the present invention is essentially equivalent to the HDL cholesterol assays performed by the conventional, but more time consuming, precipitation and centrifugation methods.

TABLE I

| Sample | Total Cholesterol (mg/dL) | HDL Cholesterol (mg/dL) |
|---|---|---|
| Comparing Methods of Assaying for HDL Cholesterol | | |
| | HDL Cholesterol by Prior Art Method | |
| Sigma Low - HDL Control Range[1] | 116–144 | 22–32 |
| Sigma High - HDL Control Range[1] | 180–224 | 57–69 |
| Hektoen Samples[2] | | |
| #1 | 406 | 56 |
| #2 | 259 | 35 |
| #3 | N/A | N/A |
| #4 | N/A | N/A |
| Comparison of HDL Cholesterol Assay Results | | |
| | OPTIMATE Results[3] | |
| Sigma Low - HDL Control Range[1] | 119.1 | 22.2 |
| Sigma High - HDL Control Range[1] | 192.1 | 64.8 |
| Hektoen Samples[2] | | |
| #1 | 415.5 | 57.0 |
| #2 | 268.2 | N/A |
| #3 | 228.3 | 31.7 |
| #4 | 182.1 | 22.7 |

[1] A sample of known HDL cholesterol concentration available from Sigma Chemical Co., St. Louis, Mo.;

[2] A sample of unknown HDL cholesterol concentration available from Hektoen Institute, Chicago, IL;

TABLE I-continued

| Sample | Total Cholesterol (mg/dL) | HDL Cholesterol (mg/dL) |
| --- | --- | --- |

3)Assay utilized a device illustrated in FIG. 2; and

4)N/A means not available.

TABLE II summarizes a comparison of blood samples assayed for HDL cholesterol by a method and device of the present invention and by a prior art centrifuge method. In each of the five examples, the HDL cholesterol assay by the method and device of the present invention essentially equalled the assay result found by the prior art method.

TABLE II

Comparative Assays for HDL Cholesterol

| Sample | Present Method[6] | Conventional Centrifuge Method |
| --- | --- | --- |
| Sigma Low - HDL Control[1] | 23.0 mg/dL | 22.4 mg/dL |
| Sigma High - HDL Control[1] | 61.1 mg/dL | 65.1 mg/dL |
| MCC Low[7] | 30.8 mg/dL | 21.3 mg/dL |
| MCC High[7] | 111.3 mg/dL | 113.2 mg/dL |
| Human Unknown[8] | 25.1 mg/dL | 24.9 mg/dL |

6)method of the present invention utilizing a device illustrated in FIG. 2, wherein the device included an optional third filter pad of untreated glass fibers;

7)Multicomponent Calibrators, available from Gilford;

8)a human whole blood sample including an unknown amount of HDL cholesterol.

FIGS. 5 through 8 further show the ability of the device and method of the present invention to separate the interfering cellular components, LDL fraction and VLDL fraction from a whole blood sample in an assay for HDL cholesterol. FIGS. 5 through 8 are plots of electrophoresis data showing that the LDL and VLDL fractions have been removed from a whole blood sample by the method and device of the present invention. The filtered plasma or serum also is essentially free of cellular components as demonstrated by the pale straw color of the filtered plasma or serum.

Figure 5:
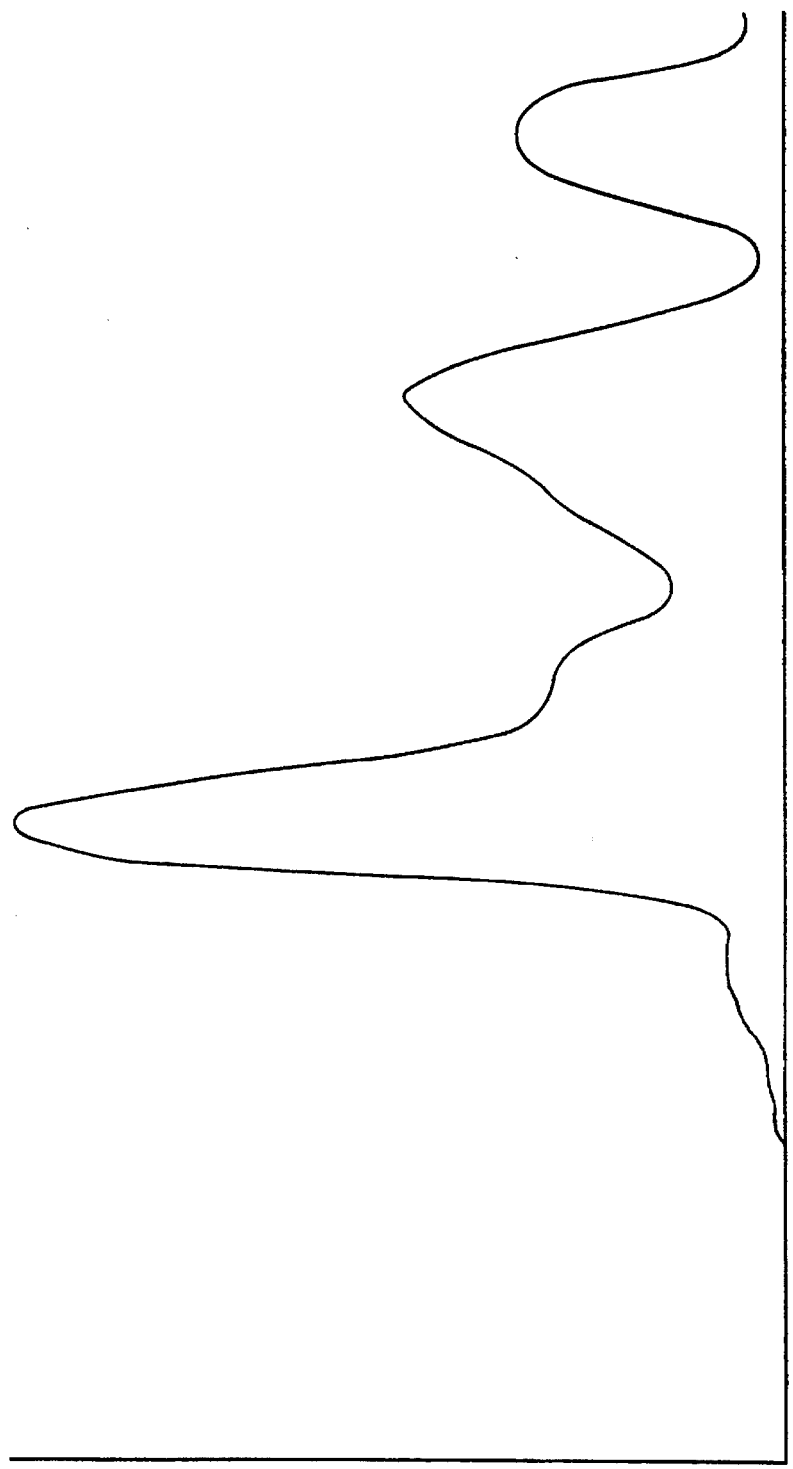
FIGS. 5 through 8 are plots showing the lipoprotein fractions present in unfiltered serum and in serum wherein the VLDL and LDL fractions are separated either by precipitation or by a device of the present invention.
Figure 8:
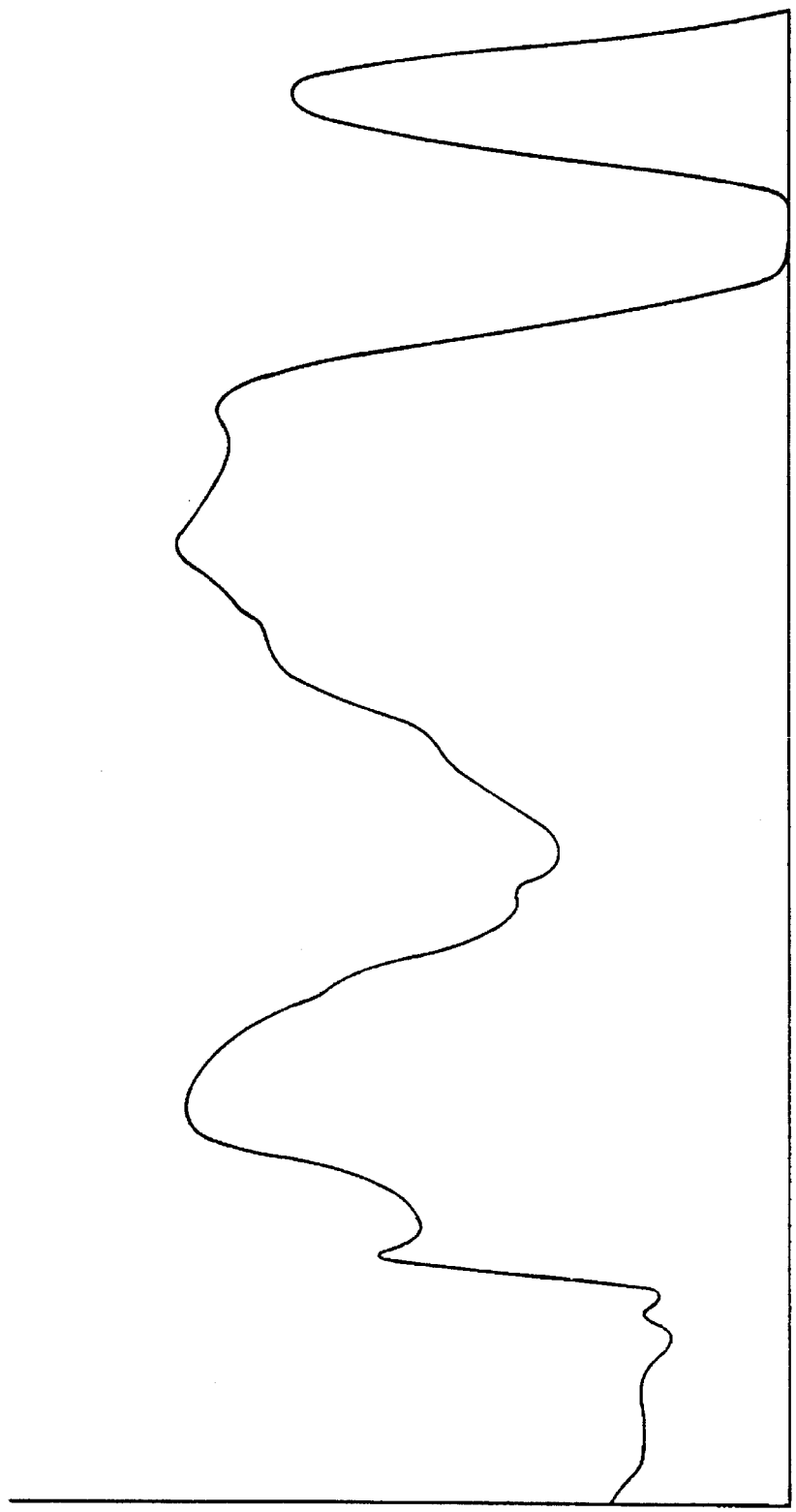

In particular, FIG. 5 is a plot of electrophoresis data from a lipoprotein scan on serum or plasma that has been separated from the cellular components of whole blood by a first separation zone that did not incorporate an optional agglutinin. FIG. 5 shows that the serum or plasma includes a VLDL fraction, an LDL fraction and an HDL fraction. In addition, FIG. 8 shows that incorporating the lectin from Solanum tubersum (potato lectin) into the first separation zone to facilitate the removal of cellular components from the plasma or serum does not effect any of the three soluble lipoprotein fractions present in the plasma or serum. Accordingly, incorporating an optional lectin into the first separation zone does not adversely affect the subsequent assay for HDL cholesterol in the whole blood sample.

Figure 6:
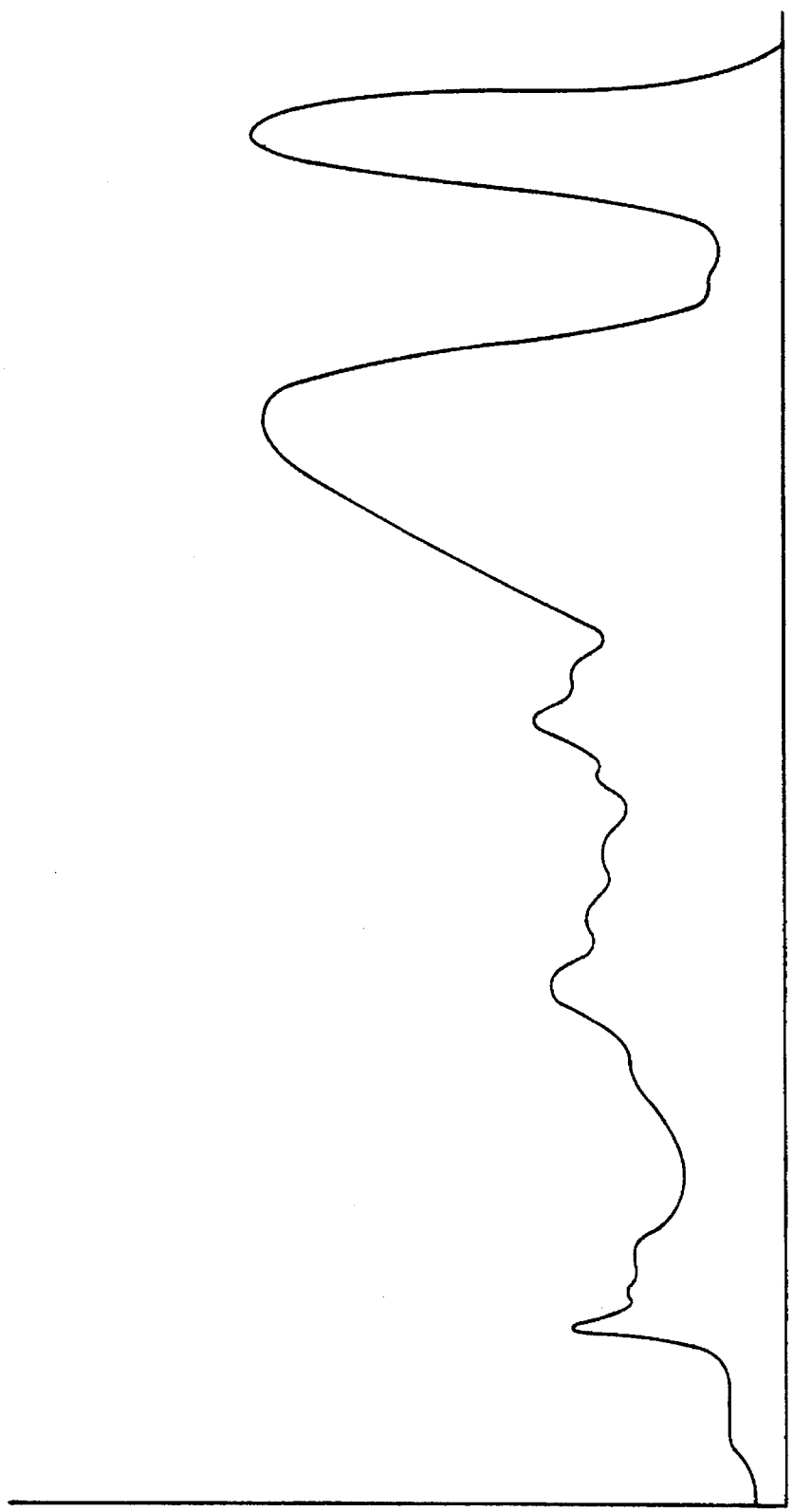
Figure 7:
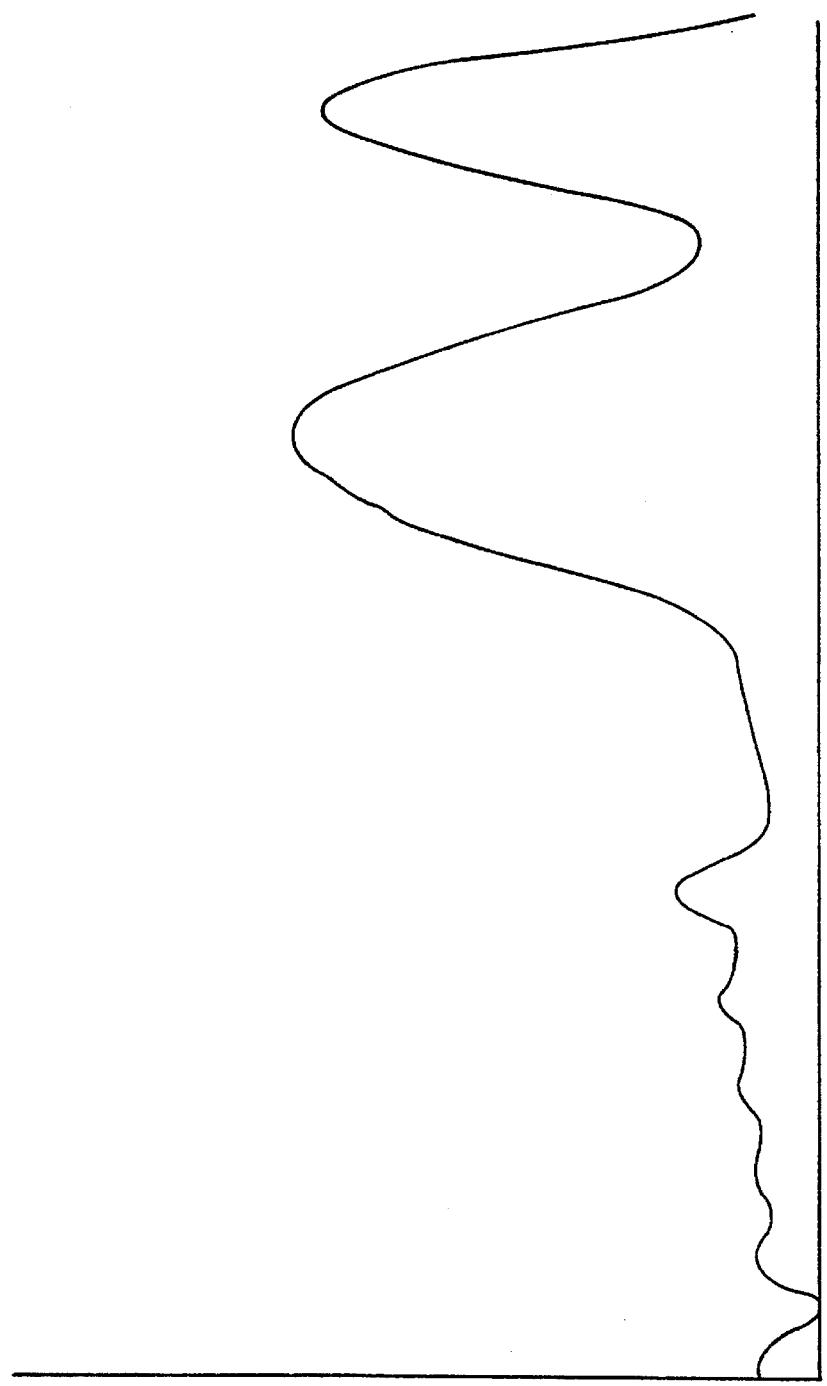

FIG. 6 is a plot of electrophoresis data from a lipoprotein scan on a plasma or serum sample that had the LDL and VLDL fractions removed by a prior art precipitation and centrifugation method. FIG. 6 illustrates that the bands attributed to the LDL and the VLDL fractions are absent. FIG. 7 is a plot of electrophoresis data from a lipoprotein scan on a plasma or serum sample that was collected after emerging from a device of the present invention, such as a device illustrated in FIG. 2. The plot in FIG. 7 also illustrates that the bands attributed to the LDL and the VLDL fractions are absent. The plot in FIG. 7 is essentially identical to the plot in FIG. 6, thereby showing that the method and device of the present invention separate essentially the entire LDL and VLDL fractions from serum or plasma.

In accordance with another important feature of the present invention, it has been shown that the concentration of HDL cholesterol in a whole blood sample including up to about 65% hematocrit can be determined accurately, and without correction, by using the method and device of the present invention. As shown in FIG. 5 and FIG. 8, the carrier matrix of the first separation zone, preferably including an optional agglutinin or coagulant, effectively separated the cellular components from the plasma or serum, without adversely affecting the concentration of the soluble lipoprotein fractions in serum or plasma. Therefore, the present invention provides an economical device and method of assaying for HDL cholesterol that is independent of the amount of hematocrit in the test sample and that provides more reproducible assay results. The device and method of the present invention demonstrate the effective removal of assay interferences followed by fast, safe, economical and accurate detection of the assay response to HDL cholesterol by currently available instrumental, or alternatively visual, detection techniques.

In accordance with yet another important feature of the present invention, the first separation zone of the test device effectively separated the cellular components of whole blood from the plasma or serum even in the presence of anticoagulants, provided that the first separation zone includes a lectin, a thrombin, a thrombin-like compound or a combination thereof. Specifically, whole blood containing anticoagulants, such as heparin or ethylenediaminetetraacetic acid (EDTA), is amenable to the separation method and the device of the present invention. Therefore, fresh blood samples can be treated with an anticoagulant, then assayed for HDL cholesterol by the process and device of the present invention at a later date.

In addition to an unexpectedly efficient separation of the red blood cells, the LDL fraction and the VLDL fraction from the plasma or serum, the process and device of the present invention allow a sufficiently large and assayable amount of plasma or serum to reach the test area of the test device. Furthermore, the plasma or serum reaches the test area of the test device in an essentially unaltered form. Generally, in the case of a dry phase test strip, the proper amount of serum or plasma has reached the test area when the test pad is saturated with plasma or serum. This is accomplished either by using a sufficiently large whole blood sample to assure plasma or serum saturation of the test pad, or, preferably, by adjusting the relative sizes of the separation zones in the separation area and the test pad such that the test pad is saturated with plasma or serum. A precisely-measured whole blood sample volume is not necessary. This process allows an essentially fixed amount of plasma or serum to reach the test pad, and renders a more accurate soluble constituent determination. The variables of blood sample size, size of filter pads, test pad size and the amount of the indicator reagent composition impregnated into the test area easily can be determined by those skilled in the art of designing diagnostic test strips.

In addition to the fast and efficient separation of the cellular components, the LDL fraction and the VLDL fraction from the serum or plasma of whole blood, and the essentially unimpeded migration of unaltered plasma or serum to the test area, the method and device of the present invention allow a quantitative assay of HDL cholesterol without dilution of the whole blood, plasma or serum, and without interference from the highly-colored red blood cells, the LDL fraction and the VLDL fraction. Testing the undiluted serum or plasma both omits a manipulative step and, more importantly, eliminates the possibility of technician error and technician contact with the potentially-infectious test sample.

A suitable chromogenic reagent composition is incorporated into the test area of the device in a sufficient amount to allow a detectable interaction with the HDL cholesterol in the freshly separated and undiluted plasma or serum. The extent of the chromogenic reaction, and therefore the quantitative amount of the HDL cholesterol, then is determined by chromogenic detection techniques, either visual or instrumental, that are well-known in the art. Accordingly, the method and test device demonstrate appreciable advantages over the prior art methods and devices because the test device and method are more economical and produce more reproducible results; the assay is independent of the hematocrit value of the test sample; the technician is not required to perform manipulative steps and potential technician errors are avoided; and the technician avoids physical contact with the blood sample.

Therefore, an accurate and reliable assay of a small volume of whole blood for HDL cholesterol is achieved within minutes, without interference by the cellular components of the whole blood, or by the soluble LDL or VLDL fractions. The assay is simple, economical and safe because additional manipulative steps, like dilution or centrifugation, are unnecessary. Furthermore, the device and method are safe because the technician is effectively protected from inadvertent contact with the potentially-infectious whole blood sample. In the case of a dry phase test strip, the entire whole blood sample, both the separated components in the separation area and the plasma or serum in the test pad, is retained by the elements of the test device. Therefore, human contact with the whole blood sample is essentially precluded. Such a feature is new in the art because prior art methods and devices for testing serum or plasma led to the possibility of human contact with the blood sample, either in wiping or rinsing of the separated components from the test device or in blood transfers and dilutions in centrifuging and related physical separation methods.

Examples 3 and 4 demonstrate assays performed in accordance with the method and test device of the present invention to assay for HDL cholesterol.

EXAMPLE 3

DETERMINATION OF HDL CHOLESTEROL IN PLASMA OR SERUM

An undiluted whole blood sample is assayed for HDL cholesterol by a test device as illustrated in FIG. 2. Similarly, an undiluted whole blood sample can be assayed for HDL cholesterol by a test device as illustrated in FIGS. 1 and 3. The whole blood sample, such as a pinprick amount, is introduced to the sample port of the device, and the whole blood sample is absorbed by a first filter pad comprising a carrier matrix preferably incorporating an optional separating reagent composition including a lectin. The blood sample chromatographs through the first filter pad, whereby the cellular components of the whole blood are separated from the plasma or serum. The blood sample is of sufficient size such that after chromatographing through the first filter pad, the amount of serum or plasma in the sample is sufficient to completely wet, or saturate, a second filter pad that is in contact with the first filter pad. The second filter pad comprises a carrier matrix incorporating a precipitating reagent composition comprising a polyvalent metal ion, preferably a divalent metal ion, and a precipitating compound. The plasma or serum chromatographs through the second filter pad, whereby the soluble LDL and VLDL fractions are separated from the plasma or serum. The plasma or serum sample is of a sufficient size such that after chromatographing through the second filter pad, the amount of serum or plasma is sufficient to fill and migrate through a capillary and be collected in the test area of the device. A reagent composition comprising the necessary reagents to assay for HDL cholesterol, and previously incorporated into the test area of the test device, interacts with the HDL cholesterol in the serum or plasma to produce a measurable chromogenic change that correlates quantitatively to the HDL cholesterol content in the serum or plasma.

The chromogenic change in the test area is determined visually, such as by a comparison to a standardized color chart, or, alternatively, instrumentally, such as by a reflectance measuring instrument. The method provides a response to the concentration of the HDL cholesterol in an undiluted serum or plasma sample without interference from the insoluble cellular components of the whole blood sample or from the soluble LDL or VLDL fractions in serum or plasma. Furthermore, the assay is independent of the hematocrit value of the whole blood sample.

EXAMPLE 4

DETERMINATION OF HDL CHOLESTEROL IN PLASMA OR SERUM BY A DRY PHASE TEST STRIP

Undiluted whole blood samples are assayed for HDL cholesterol content by using dry phase test devices as illustrated in FIG. 4. Each test device includes a test pad comprising a substrate material of either a polyamide, such as nylon, like BIODYNE B, having a 3µ micron pore size and available from Pall Corporation, or a polyvinylidene fluoride, like DURAPORE, having a 0.65µ pore size, available from Millipore Corporation, Bedford, Mass. The substrate material of the test pad incorporates a reagent composition first by immersing the substrate material into an aqueous solution including about 1.5% (w/w) tetramethylbenzidene hydrochloride indicator dye, and about 0.4% (w/w) poly(methyl vinyl ether/maleic anhydride) (GANTREZ AN139, available from GAF Chemicals Corp., Wayne, N.J.). The impregnated substrate material then is dried in a hot air convection oven at about 50° C. for about 5 minutes to about 10 minutes. The impregnated substrate material then is immersed in a second aqueous solution including:

| | |
|---|---|
| 0.2 M Phosphate Buffer (pH 6.0) | 67.9% (w/w) |
| Glycerol | 6.4% (w/w) |
| Sodium taurocholate | 0.7% (w/w) |
| Peroxidase | 500 U/mL |
| Cholesterol Esterase | 500 U/mL |
| Cholesterol Oxidase | 250 U/mL |
| Polyvinylpyrrolidone (PVP K-60 available from GAF Chemicals Corp., Wayne, NJ) (45% w/w) | 23.8% (w/w) |

After the second impregnation, the substrate material again is dried in a hot air convection oven at about 50° C. for from about 5 minutes to about 10 minutes to provide a test pad to determine the amount of cholesterol in a liquid test sample.

Each test device also includes a first filter pad comprising a carrier matrix incorporating a separating reagent composition including a lectin; and includes a second filter pad comprising a carrier matrix incorporating a precipitating reagent composition comprising a divalent metal ion and a precipitating compound. The carrier matrix of the first and the second filter pad is a glass fiber matrix having a pore size of from about 1μ to about 6μ, and available from Whatman Ltd. or Millipore Corporation. The first filter pad is immersed into an aqueous separating reagent composition including about 0.05% (w/w) of the lectin from Phytolacca Americana. The second filter pad is immersed into an aqueous precipitating reagent composition including about 500 mM magnesium chloride and about 10 g/L dextran sulfate.

After incorporating the separating reagent composition and the precipitating reagent composition into their respective glass fiber matrix, each impregnated glass fiber matrix is scraped with a glass rod to remove any excess separating reagent composition or precipitating reagent composition. The impregnated glass fiber matrices then are dried in a hot air convection oven at about 50° C. for about 30 minutes to provide a first filter pad and a second filter pad of the present invention.

The test pad and the first and second filter pads then are positioned in a laminar array on a transparent handle as illustrated in FIG. 4. The resulting test pad is used to assay whole blood samples for HDL cholesterol. Each assay requires approximately 30 μl of whole blood sample and one test device of the present invention.

The assays are performed by first making a small puncture wound in any part of the body. The first filter pad of the test device then contacts whole blood seeping from the puncture. After a sufficient amount of whole blood saturates the first filter pad, the test device is removed from the wound. The whole blood sample then is absorbed sufficiently into the first and second filter pads such that excess whole blood sample does not remain in a pool on any outside surface of the test device. After a sufficient time, such as about one to two minutes, the test pad is examined through the transparent handle in a reflectance measuring instrument, i.e., an OPTIMATE instrument, available from Miles, Inc., Elkhart, Ind. Alternatively, the test device is examined visually, such as by visually comparing the test pad to a standardized color chart. After examining the test pad for a response, the test pad is discarded. The method and test device precludes the technician from contacting any surface containing the potentially-infectious whole blood sample.

The color transition resulting from an interaction between the serum or plasma including the HDL fraction with the indicator reagent composition incorporated into the test pad is examined by reflectance photometry. In general, comparison of the color transition resulting from contacting a test pad with a blood sample of unknown HDL cholesterol concentration to the color transition resulting from a test pad contacting a standardized HDL cholesterol concentration gives a quantitative assay for the HDL cholesterol concentration in the blood sample. Then, a dose response plot is graphed to demonstrate that the intensity of the color transition of the assay varied in direct proportion to the HDL cholesterol concentration of the test sample.

It will be understood that the present disclosure has been made only by way of preferred embodiment and that numerous changes in details of construction, combination, and arrangement of parts can be resorted to without departing from the spirit and scope of the invention as hereunder claimed.

What is claimed is:

1. A method of separating cellular components, low density lipoprotein fraction and very low density lipoprotein fraction from an undiluted whole blood sample consisting essentially of:

(a) first directly contacting the undiluted whole blood sample with a first carrier matrix to separate the cellular components of the whole blood sample and provide a plasma or serum, wherein said first carrier matrix has incorporated therein about 25 to about 250 units of an agglutinin, about 50 to about 150 NIH units of a coagulant or a mixture thereof to agglutinize or coagulate the cellular components of the undiluted whole blood sample in the first carrier matrix;

(b) then allowing the plasma or serum to migrate by gravity to a second carrier matrix that has the same dimensions and is in fluid communication with the first carrier matrix to separate the low density lipoprotein fraction and the very low density lipoprotein fraction from the plasma or serum, said second carrier matrix having a pore size of at least 1 to about 50 microns and having incorporated therein a precipitating reagent composition comprising a sufficient amount of a polyvalent metal ion and a sufficient amount of a precipitating compound to separate the low density lipoprotein fraction and the very low density lipoprotein fraction from the plasma or serum and to provide a serum or plasma including a high density lipoprotein fraction, wherein the precipitating compound is selected from the group consisting of dextran sulfate, heparin sodium, phosphotungstic acid, polyvinyl sulfate, sodium tungstate, ammonium molybdate, and mixtures thereof; and (c) then allowing the serum or plasma including the high density lipoprotein fraction to flow by gravity through the second carrier matrix.

2. The method of claim 1 further comprising treating the plasma or serum including the high density lipoprotein fraction that exits the second carrier matrix to assay for the presence or concentration of a predetermined constituent of the high density lipoprotein fraction, wherein said assay is independent of the amount of hematocrit in the whole blood sample.

3. The method of claim 1 wherein the agglutinin is a nonblood specific lectin selected from the group consisting of *Abrus precatorius* (abrin, Jequirty bean), *Agaricus bisporous* (mushroom), *Bauhinia purpurea* (camels foot tree), *Caragana arborescens* (Siberian pea tree), *Cicer arietinum* (chick pea), *Codium fragile* (Green marine algae), *Canavalia ensiformis* (Con A, Concanavalin A. Jack bean), *Datura stramonium* (jimson weed), *Glycine max* (Soybean), *Lathyrus odoratus* (Sweet Pea), *Lens culinaris* (Lentil), *Limulus polyphemus* (Horseshoe crab, Limulin), *Lycopersicon esculentum* (Tomato), *Maclura pomifera* (Osage orange), *Mycoplasma gallisepticum*, *Naja mocambique mocambique* (cobra venom), *Naja Naja kaouthia* (cobra venom), *Perseau americana* (Avocado), *Phaseolus coccineus* (Scarlet runner bean), *Phaseolus vulgaris* (Red Kidney bean), *Phytolacca americana* (Pokeweed), *Pisum sativum* (garden pea), *Pseudomonas aeruginosa, Psophocarpus tetragonolobus* (winged bean), *Robinia pseudoacacia* (Black locust, false locust), *Sambucus nigra* (elder), *Solanum tuberosum* (Potato), *Triticum vulgaris* (Wheat germ), *Vicia faba* (fava bean, broad bean), *Vicia sativa, Vigna radiata* (Mung bean), *Viscum album* (European mistletoe), *Wisteria floribunda* (Japanese wisteria) and mixtures thereof.

4. The method of claim 1 wherein the coagulant is selected from the group consisting of bovine thrombin, human thrombin, horse thrombin, goat thrombin, mouse thrombin, rat thrombin, pig thrombin, sheep thrombin, agkistrodon contortrix, ancrod, atroxin, crotalase, and mixtures thereof.

5. A method of separating plasma or serum that is essentially free of cellular components, low density lipoproteins and very low density lipoproteins, from an undiluted whole blood sample and assaying the plasma or serum for a predetermined constituent of high density lipoproteins present in the plasma or serum consisting essentially of:

(a) first directly contacting the undiluted whole blood sample with a first carrier matrix to separate the cellular components of the whole blood sample and to provide a plasma or serum, wherein said first carrier matrix has incorporated therein a separating reagent composition comprising about 25 to about 250 units an agglutinin, about 50 to about 150 NIH units of a coagulant or a mixture thereof to agglutinize or coagulate the cellular components of the undiluted whole blood sample in the first carrier matrix;

(b) then allowing the plasma or serum to migrate by gravity to a second carrier matrix that has the same dimensions and is in fluid communication with the first carrier matrix to separate the low density lipoproteins and the very low density lipoproteins from the plasma or serum, said second carrier matrix having a pore size of at least 1 to about 50 microns and having incorporated therein a precipitating reagent comprising a sufficient amount of a polyvalent metal ion and a sufficient amount of a precipitating compound to separate the low density lipoproteins and the very low density lipoproteins from the plasma or serum and to provide a serum or plasma that is essentially free of cellular components, low density lipoproteins and very low density lipoproteins and that includes high density lipoproteins, wherein the precipitating compound is selected from the group consisting of dextran sulfate, heparin sodium, phosphotungstic acid, polyvinyl sulfate, sodium tungstate, ammonium molybdate, and mixtures thereof;

(c) then allowing the serum or plasma including the high density lipoproteins to flow by gravity through the second carrier matrix to contact a test area incorporating a reagent composition to assay for the predetermined constituent of the high density lipoproteins in the plasma or serum, said reagent composition capable of interacting with the predetermined constituent of the high density lipoprotein to produce a detectable change in the test area; and (d) examining the test area for a detectable change, wherein the assay is independent of the amount of hematocrit present in the whole blood sample.

6. The method of claim 5 wherein the first carrier matrix is selected from the group consisting of inorganic powders, sponge materials, argillaceous substances, cloth, hydrophilic naturally-occurring polymers, hydrophilic naturally-occurring modified polymers, hydrophilic synthetic polymers, cellulosic materials, glass fibers, and mixtures thereof.

7. The method of claim 5 wherein the first carrier matrix is selected from the group consisting of silica gel, alumina, diatomaceous earth, filter paper, chromatographic paper, glass fiber, dellulose acetate, cellulosic beads, polyvinyl chloride, polyacrylamide, polyacrylate, polyurethane, crosslinked dextran, agarose, polyethylene, polypropylene, nylon, polyvinylidene fluoride, polysulfone, and mixtures thereof.

8. The method of claim 5 wherein the first carrier matrix has a pore size in the range of from about 0.1 micron to about 50 microns.

9. The method of claim 5 wherein the agglutinin is a nonblood specific lectin selected from the group consisting of *Abrus precatorius* (abrin, Jequirty bean), *Agaricus bisporous* (mushroom), *Bauhinia purpurea* (camels foot tree), *Caragana arborescens* (Siberian pea tree), *Cicer arietinum* (chick pea), *Codium fragile* (Green marine algae), *Canavalia ensiformis* (Con A, Concanavalin A, Jack bean), *Datura stramonium* (jimson weed), *Glycine max* (Soybean), *Lathyrus odoratus* (Sweet Pea), *Lens culinaris* (Lentil), *Limulus polyphemus* (Horseshoe crab, Limulin), *Lycopersicon esculentum* (Tomato), *Maclura pomifera* (Osage orange), *Mycoplasma gallisepticum, Naja mocambique mocambique* (cobra venom), *Naja Naja kaouthia* (cobra venom), *Perseau americana* (Avocado), *Phaseolus coccineus* (Scarlet runner bean), *Phaseolus vulgaris* (Red Kidney bean), *Phytolacca americana* (Pokeweed), *Pisum sativum* (garden pea), *Pseudomonas aeruginosa, Psophocarpus tetragonolobus* (winged bean), *Robinia pseudoacacia* (black locust, false locust), *Sambucus nigra* (elder), *Solanum tuberosum* (Potato), *Triticum vulgaris* (Wheat germ), *Vicia faba* (fava bean, broad bean), *Vicia sativa, Vigna radiata* (Mung bean), *Viscum album* (European mistletoe), *Wisteria floribunda* (Japanese wisteria) and mixtures thereof.

10. The method of claim 5 wherein the coagulant is selected from the group consisting of bovine thrombin, human thrombin, horse thrombin, goat thrombin, mouse thrombin, rat thrombin, pig thrombin, sheep thrombin, agkistrodon contortrix, ancrod, atroxin, crotalase, and mixtures thereof.

11. The method of claim 5 wherein the second carrier matrix is selected from the group consisting of inorganic powders, sponge materials, argilllaceous substances, cloth, hydrophilic naturally-occurring polymers, hydrophilic naturally-occurring modified polymers, hydrophilic synthetic polymers, cellulosic materials, glass fibers, and mixtures thereof.

12. The method of claim 5 wherein the second carrier matrix is selected from the group consisting of silica gel, alumina, diatomaceous earth, filter paper, chromatographic paper, glass fiber, cellulose acetate, cellulosic beads, polyvinyl chloride, polyacrylamide, polyacrylate, polyurethane, crosslinked dextran, agarose, polyethylene, polypropylene, nylon, polyvinylidene fluoride, polysulfone, and mixtures thereof.

13. The method of claim 5 wherein the polyvalent metal ion is a divalent metal ion.

14. The method of claim 13 wherein the divalent metal ion is selected from the group consisting of magnesium, calcium, manganese, cobalt, strontium, zinc, barium, copper, and mixtures thereof.

15. The method of claim 5 wherein the polyvalent metal ion is selected from the group consisting of aluminum, iron, chromium, magnesium, calcium, manganese, cobalt, strontium, zinc, barium, copper, and mixtures thereof.

16. The method of claim 5 wherein the precipitating reagent includes about 10 to about 1000 millimoles per liter of the polyvalent metal ion and about 0.1 to about 20 grams per liter of the precipitating compound.

17. The method of claim 5 wherein the predetermined constituent of the high density lipoproteins is cholesterol.

18. The method of claim 5 further comprising allowing the serum or plasma including the high density lipoproteins to flow through a third carrier matrix prior to contacting the test area.

* * * * *